US008262867B2

(12) United States Patent
Dutta et al.

(10) Patent No.: US 8,262,867 B2
(45) Date of Patent: Sep. 11, 2012

(54) METAL ALKOXIDES, APPARATUS FOR MANUFACTURING METAL ALKOXIDES, RELATED METHODS AND USES THEREOF

(75) Inventors: Partha S. Dutta, Clifton Park, NY (US); Sarah L. Lewis, Delmar, NY (US); Kyle E. Litz, Ballston Spa, NY (US); Mark N. Rossetti, Castleton, NY (US); Tracey M. Jordan, Valley Falls, NY (US); Jennifer L. Vreeland, Troy, NY (US)

(73) Assignee: Auterra, Inc., Malta, NY (US)

( * ) Notice: Subject to any disclaimer, the term of this patent is extended or adjusted under 35 U.S.C. 154(b) by 0 days.

(21) Appl. No.: 12/731,524

(22) Filed: Mar. 25, 2010

(65) Prior Publication Data

US 2010/0179339 A1 Jul. 15, 2010

Related U.S. Application Data

(62) Division of application No. 12/262,851, filed on Oct. 31, 2008.

(51) Int. Cl.
*B01D 3/34* (2006.01)
*B01J 8/00* (2006.01)
*C07C 29/70* (2006.01)
*C09K 21/06* (2006.01)
*C07F 5/02* (2006.01)
*C07F 5/06* (2006.01)
*C07F 3/06* (2006.01)

(52) U.S. Cl. ....... 203/38; 203/64; 203/DIG. 6; 252/601; 422/187; 556/2; 556/7; 556/27; 556/171; 556/172

(58) Field of Classification Search ............. 203/38, 203/64, DIG. 6; 422/187; 556/2, 7, 27, 171, 556/172, 181; 75/330; 252/601
See application file for complete search history.

(56) References Cited

U.S. PATENT DOCUMENTS

| 2,085,924 | A | 7/1937 | Riegler |
| 2,301,204 | A | 11/1942 | Fields et al. |
| 2,643,262 | A | 6/1953 | Bostwick |
| 2,666,076 | A | 1/1954 | Rex et al. |
| 2,796,443 | A | 6/1957 | Meyer et al. |
| 2,987,537 | A | 6/1961 | McCloskey et al. |
| 3,030,274 | A | 4/1962 | Grant |
| 3,062,685 | A | 11/1962 | Sanford et al. |
| 3,072,704 | A | 1/1963 | Carpenter et al. |
| 3,119,852 | A | 1/1964 | Gilsdorf |

(Continued)

FOREIGN PATENT DOCUMENTS

EP 0091425 A2 12/1983

(Continued)

OTHER PUBLICATIONS

Hazimah et al., Some Complexes of Glycerol and their Applications, Palm Oil Development vol. 35 pp. 8-10 2001.

(Continued)

*Primary Examiner* — Virginia Manoharan
(74) *Attorney, Agent, or Firm* — Schmeiser, Olsen & Watts, LLP

(57) ABSTRACT

Compounds, synthesis of, and methods for synthesizing metal alkoxide derivatives; and metal alkoxide derivatives for use as flame retardants are described. Group 13 metal alkoxides having flame retardant properties may be prepared by reacting the periodic table group 13 metalloid or metal trihydroxide with an alcohol.

12 Claims, 3 Drawing Sheets

U.S. PATENT DOCUMENTS

| | | | |
|---|---|---|---|
| 3,250,732 A | 5/1966 | Bengelsdorf et al. | |
| 3,253,013 A | 5/1966 | DiCerrione et al. | |
| 3,036,918 A | 2/1967 | Schenck et al. | |
| 3,352,895 A | 11/1967 | Holbert et al. | |
| 3,413,325 A | 11/1968 | Berkheimer | |
| 3,444,226 A | 5/1969 | Schmank et al. | |
| 3,444,292 A | 5/1969 | Beekman et al. | |
| 3,476,522 A | 11/1969 | Stoval | |
| 3,480,596 A | 11/1969 | Holmes | |
| 3,487,095 A | 12/1969 | Nannelli et al. | |
| 3,629,229 A | 12/1971 | Schmank | |
| 3,686,249 A | 8/1972 | Hartmann | |
| 3,752,834 A | 8/1973 | Bardinet et al. | |
| 3,792,070 A | 2/1974 | Jones et al. | |
| 3,819,671 A | 6/1974 | Bouillon et al. | |
| 3,856,839 A | 12/1974 | Smith et al. | |
| 3,929,986 A | 12/1975 | Bouillon et al. | |
| 4,021,464 A | 5/1977 | Mayerhofer et al. | |
| 4,052,428 A | 10/1977 | Lerner et al. | |
| 4,052,429 A | 10/1977 | Merkl | |
| 4,087,402 A | 5/1978 | Monte et al. | |
| 4,113,757 A | 9/1978 | Kay | |
| 4,166,536 A | 9/1979 | Roberts et al. | |
| 4,230,822 A | 10/1980 | Murch et al. | |
| 4,242,271 A | 12/1980 | Weber et al. | |
| 4,288,410 A | 9/1981 | Weber et al. | |
| 4,298,753 A | 11/1981 | Schinabeck et al. | |
| 4,349,494 A | 9/1982 | Fulmer | |
| 4,524,201 A | 6/1985 | Barnabeo et al. | |
| 4,544,761 A | 10/1985 | Taylor et al. | |
| 4,557,843 A * | 12/1985 | Holstedt et al. | 508/196 |
| 4,590,289 A | 5/1986 | Albert et al. | |
| 4,609,746 A | 9/1986 | Barfurth et al. | |
| 4,626,596 A | 12/1986 | Marquis et al. | |
| 4,681,959 A | 7/1987 | Ayen et al. | |
| 4,687,868 A | 8/1987 | Shum et al. | |
| 4,705,764 A | 11/1987 | Matsumoto | |
| 4,722,919 A | 2/1988 | Marquis et al. | |
| 4,745,204 A | 5/1988 | Cuomo et al. | |
| 4,751,318 A | 6/1988 | Summers, III et al. | |
| 4,767,875 A | 8/1988 | Vincenti et al. | |
| 4,789,752 A | 12/1988 | Kotzsch et al. | |
| 4,810,810 A | 3/1989 | Kramer et al. | |
| 4,822,876 A | 4/1989 | Wright et al. | |
| 4,835,298 A | 5/1989 | Terbot et al. | |
| 5,120,805 A | 6/1992 | Woodson et al. | |
| 5,139,976 A * | 8/1992 | Terbot et al. | 501/12 |
| 5,142,074 A | 8/1992 | Treacy et al. | |
| 5,194,069 A | 3/1993 | Someus | |
| 5,276,219 A | 1/1994 | Schwinderman et al. | |
| 5,409,683 A * | 4/1995 | Tillotson et al. | 423/338 |
| 5,646,324 A | 7/1997 | Matkin et al. | |
| 5,710,086 A | 1/1998 | Brunelle et al. | |
| 5,914,417 A | 6/1999 | Reichert et al. | |
| 6,025,503 A | 2/2000 | Mikami et al. | |
| 6,323,356 B1 | 11/2001 | Lowenberg et al. | |
| 6,350,395 B1 | 2/2002 | Kuemin | |
| 6,355,821 B1 | 3/2002 | Koplick et al. | |
| 6,444,862 B1 | 9/2002 | Burkhardt et al. | |
| 6,469,189 B1 | 10/2002 | Kadokura et al. | |
| 6,548,685 B2 | 4/2003 | Zell | |
| 6,603,033 B2 | 8/2003 | Woo | |
| 6,759,560 B2 | 7/2004 | Guth et al. | |
| 6,953,863 B2 | 10/2005 | Pratt et al. | |
| 7,273,943 B2 | 9/2007 | Reuter et al. | |
| 7,449,496 B2 * | 11/2008 | Jin et al. | 518/700 |
| 2003/0023105 A1 | 1/2003 | Burkhardt et al. | |
| 2003/0127020 A1 | 7/2003 | Smith et al. | |
| 2004/0220426 A1 | 11/2004 | Yada et al. | |
| 2004/0227130 A1 * | 11/2004 | Hoerold et al. | 252/601 |
| 2006/0208215 A1 | 9/2006 | Metzner et al. | |
| 2007/0056468 A1 | 3/2007 | Reuter et al. | |
| 2007/0129571 A1 | 6/2007 | Yada et al. | |

FOREIGN PATENT DOCUMENTS

| | | |
|---|---|---|
| EP | 1452518 A1 | 1/2004 |
| JP | 04239059 | 8/1992 |

OTHER PUBLICATIONS

Katz et al. Handbook of Fillers for Plastics (p. 292 and p. 294 1st column Section 3.1, 2nd full paragraph) 1987 Van Nostrand Reinhold New York {Chpt 16 by Sobolev et al.}

Office Action (Mail Date Jul. 13, 2010) for U.S. Appl. No. 12/731,693, filed Mar. 25, 2010.

Office Action (Mail Date Jul. 9, 2010) for U.S. Appl. No. 12/731,775, filed Mar. 25, 2010.

Application No. PCT/US2008/82380, International Search Report and the Written Opinion of the International Searching Authority, or the Declaration dated Mar. 16, 2009. 13 pages.

Office Action (Mail Date Jul. 7, 2009) for U.S. Appl. No. 12/262,851, filed Oct. 31, 2008.

Office Action (Mail Date Jan. 25, 2010) for U.S. Appl. No. 12/262,851, filed Oct. 31, 2008.

Office Action (Mail Date Jan. 5, 2011) for U.S. Appl. No. 12/731,593, filed Mar. 25, 2010.

Office Action (Mail Date Mar. 7, 2011) for U.S. Appl. No. 12/731,775, filed Mar. 25, 2010.

Office Action (Mail Date May 4, 2010) for U.S. Appl. No. 12/262,851, filed Oct. 31, 2008.

Office Action (Mail Date Sep. 22, 2010) for U.S. Appl. No. 12/262,851, filed Oct. 31, 2008.

Application No. EP08 85 3241 European Search Report dated Jul. 26, 2011. 11 pages.

* cited by examiner

METAL ALKOXIDES, APPARATUS FOR MANUFACTURING METAL ALKOXIDES, RELATED METHODS AND USES THEREOF

CROSS-REFERENCE TO RELATED APPLICATIONS

This divisional application claims priority to U.S. patent application Ser. No. 12/262,851 filed on Oct. 31, 2008, which claims priority to U.S. Provisional Application No. 60/990, 149 filed on, Nov. 26, 2007, the entire disclosure of which are incorporated herein by reference. This application is also related by subject matter to PCT/US2008/005624, filed May 2, 2008 which claims priority to U.S. Provisional Application Nos. 60/924,214, filed on May 3, 2007, and 60/917,171, filed on May 10, 2007, the entire contents of which are incorporated herein by reference.

FIELD OF THE INVENTION

The invention generally relates to compounds, synthesis of, and methods for synthesizing metal alkoxide derivatives; and metal alkoxide derivatives for use as flame retardants. Specifically, the invention relates to reaction apparatus relating to synthesis of metal alkoxides and compounds produced therefrom and methods of use thereof.

BACKGROUND OF THE INVENTION

Metal alkoxides are useful as precursors for metal and metal oxide film deposition, such as via Chemical Vapor Deposition (CVD), and as a flame retardant additive in plastics and coatings. There currently exist regulatory mandates to eliminate the use of halogen-containing flame retardant compositions. Metal alkoxides are also known to be useful as catalysts for organic reactions. Reactions between some metal compounds and alcohols to form the corresponding metal alkoxides and acid by-product are known. However, current techniques either require large amounts of base to neutralize the acid produced and/or they use multiple process steps to perform reaction and purification of the final product. In addition, current methods are limited to batch or semi-batch processing, thus reaction equilibria can limit the extent of reaction. There exists a need for a system and method for producing metal alkoxides in high volume with efficient yield. There further exists a need for new materials having flame retardant properties

SUMMARY OF THE INVENTION

A first aspect of the present invention relates to a method comprising contacting a first amount of a metal compound and a first amount of an alcohol in a reaction-distillation zone and, resulting from said contacting, forming a metal alkoxide from a reaction of said metal compound and said alcohol;

simultaneously with said contacting, removing reaction products from a vapor phase of said reaction-distillation zone;

simultaneously with said contacting, removing reaction products from a liquid phase of said reaction-distillation zone; and simultaneously with said contacting, introducing into said reaction-distillation zone a second amount of said metal compound and a second amount of said alcohol.

A second aspect of the present invention relates to a reaction apparatus comprising:

a reactor body comprising a corrosion resistant material, said reactor body having a hollow interior;

a rotor disposed within said hollow interior of said reactor body, said rotor configured to rotate and mix reaction components within said reaction body;

a condenser disposed within said hollow interior; and a temperature regulating device disposed on an outside surface of said reactor body.

A third aspect of the present invention relates to a reaction system comprising:

a reactor comprising an acid resistant reactor body, said reactor body having a first inlet port, a first outlet port, a second outlet port, and a hollow interior, said hollow interior having a reaction-distillation zone disposed therein, said reaction-distillation zone comprising a vapor phase and a liquid phase;

a stream of reactants entering said first inlet port, said reactants comprising a metal compound and an alcohol;

a stream of vapor phase products exiting said first outlet port, said vapor phase products derived from a reaction of said metal compound and said alcohol; and a stream of liquid phase products exiting said second outlet port said liquid phase products derived from a reaction of said metal compound and said alcohol.

A fourth aspect of the present invention relates to a reaction system comprising:

a reaction apparatus comprising an acid resistant reactor body with a hollow interior having a reaction-distillation zone disposed therein, said reaction-distillation zone comprising a vapor phase and a liquid phase of a reaction between at least two reactants, said reactor body having at least one inlet port in contact with said reaction-distillation zone, a first outlet port in contact with said vapor phase, and a second outlet port in contact with said liquid phase;

a first feed vessel operably connected to said at least one inlet port, said feed vessel configured to continuously introduce said at least two reactants into said reaction-distillation zone;

a vapor phase removal device operably connected to said first outlet port, said vapor phase removal device configured to remove reaction products of said reaction from said vapor phase; and an extraction device operably connected to said second outlet port, said extraction device configured to remove reaction products from said liquid phase.

A fifth aspect of the present invention relates to a flame retardant composition comprising a metal alkoxide additive of the formula $M(OR)_x$, wherein x is an integer from 1 to 4, M is a group 13 metal, and R independently comprises a hydrogen, substituted alkyl group, unsubstituted alkyl group, substituted aryl group, unsubstituted aryl group, and/or a combination thereof.

BRIEF DESCRIPTION OF THE DRAWINGS

The features of the invention are set forth in the appended claims. The invention itself, however, will be best understood by reference to the following detailed description of illustrative embodiments when read in conjunction with the accompanying drawings.

DETAILED DESCRIPTION OF THE INVENTION

Figure 1:
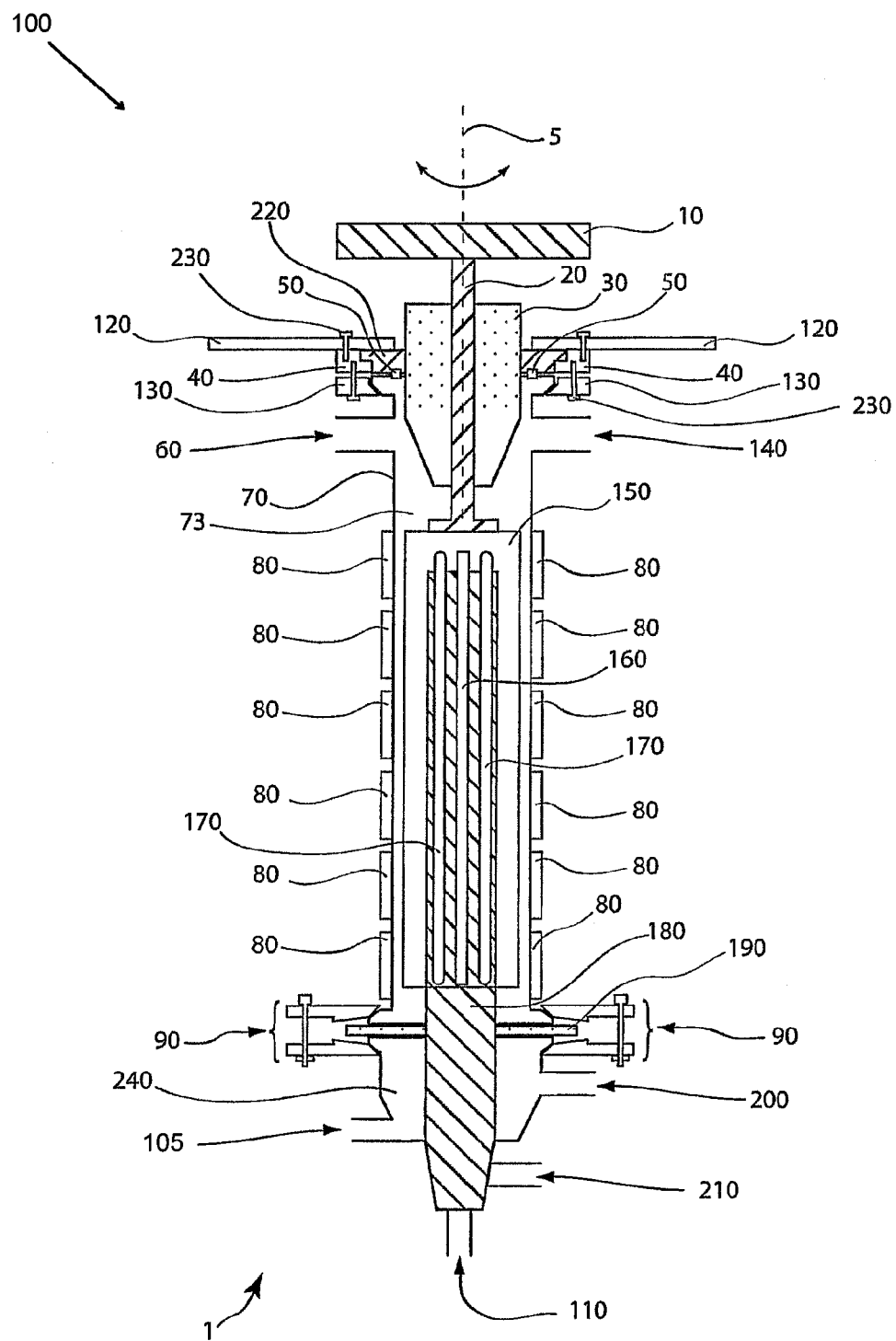
FIG. 1 is an illustration of a reaction apparatus, in accordance with embodiments of the present invention.

Although certain embodiments of the present invention will be shown and described in detail, it should be understood that various changes and modifications may be made without departing from the scope of the appended claims. The scope of the present invention will in no way be limited to the number of constituting components, the materials thereof, the shapes thereof, the relative arrangement thereof, etc., and are disclosed simply as examples of embodiments. The features and advantages of the present invention are illustrated in detail in the accompanying drawings, wherein like reference numerals refer to like elements throughout the drawings. Although the drawings are intended to illustrate the present invention, the drawings are not necessarily drawn to scale.

In general, "substituted" as used herein refers to an alkyl, cycloalkyl, cycloalkylalkyl, heterocyclyl, or heterocyclylalkyl group, as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, heterocyclyloxy, and heterocyclylalkoxy groups; carbonyls (oxo); carboxyls; esters; ethers; urethanes; alkoxyamines; thiols; sulfides; sulfoxides; sulfones; sulfonyls; sulfonamides; amines; N-oxides; isocyanates; cyanates; thiocyanates; nitro groups; nitriles (i.e., CN); and the like.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups can also be substituted with substituted or unsubstituted alkyl or alkenyl groups as defined below.

Alkyl groups include straight chain and branched alkyl groups having from 1 to about 20 carbon atoms or, in some embodiments, from 1 to 8, 1 to 6, or 1 to 4 carbon atoms. Alkyl groups further include cycloalkyl groups as defined below. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above.

Alkenyl groups include straight and branched chain and cycloalkyl groups as defined above, except that at least one double bond exists between two carbon atoms. Thus, alkenyl groups have from 2 to about 12 carbon atoms in some embodiments, from 2 to 10 carbon atoms in other embodiments, and from 2 to 8 carbon atoms in other embodiments. Examples include, but are not limited to vinyl, allyl, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, cyclohexenyl, cyclopentenyl, cyclohexadienyl, butadienyl, pentadienyl, and hexadienyl, among others. Representative substituted alkenyl groups may be mono-substituted or substituted more than once, such as, but not limited to, mono-, di- or tri-substituted with substituents such as those listed above.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include mono-, bicyclic and polycyclic ring systems. Substituted cycloalkyl groups may be substituted one or more times with non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. In some embodiments, cycloalkylalkyl groups have from 4 to 20 carbon atoms, 4 to 16 carbon atoms, and typically 4 to 10 carbon atoms. Substituted cycloalkylalkyl groups can be substituted at the alkyl, the cycloalkyl or both the alkyl and cycloalkyl portions of the group. Representative substituted cycloalkylalkyl groups can be mono-substituted or substituted more than once, such as, but not limited to, mono-, di- or tri-substituted with substituents such as those listed above.

Aryl groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups.

Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups can be mono-substituted or substituted more than once. For example, monosubstituted aryl groups include, but are not limited to, 2-, 3-, 4-, 5-, or 6-substituted phenyl or naphthyl groups, which can be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 20 carbon atoms, 7 to 14 carbon atoms or 7 to 10 carbon atoms. Substituted aralkyl groups can be substituted at the alkyl, the aryl or both the alkyl and aryl portions of the group. Representative aralkyl groups include but are not limited to benzyl and phenethyl groups and fused (cycloalkylaryl) alkyl groups such as 4-ethyl-indanyl. Representative substituted aralkyl groups can be substituted one or more times with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. In some embodiments, heterocyclyl groups include 3 to 20 ring members, whereas other such groups have 3 to 6, 3 to 10, 3 to 12, or 3 to 15 ring members. Heterocyclyl groups encompass unsaturated, partially saturated and saturated ring systems, such as, for example, imidazolyl, imidazolinyl and imidazolidinyl groups. However, the phrase "heterocyclyl group" does not include heterocyclyl groups that have other groups, such as alkyl, oxo or halo groups, bonded to one of the ring members. Rather, these are referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups can be mono-substituted or substituted more than once, such as, but not limited to, pyridyl or morpholinyl groups, which are 2-, 3-, 4-, 5-, or 6-substituted, or disubstituted with various substituents such as those listed above.

Heterocyclylalkyl groups are alkyl groups as defined above in which a hydrogen or carbon bond of an alkyl group is replaced with a bond to a heterocyclyl group as defined above. Substituted heterocyclylalkyl groups can be substituted at the alkyl, the heterocyclyl or both the alkyl and heterocyclyl portions of the group. Representative heterocyclyl alkyl groups include, but are not limited to, 4-ethyl-morpholinyl, 4-propylmorpholinyl, furan-2-yl methyl, furan-3-yl methyl, pyridine-3-yl methyl, tetrahydrofuran-2-yl ethyl, and indol-2-yl propyl. Representative substituted heterocyclylalkyl groups can be substituted one or more times with substituents such as those listed above.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups can be substituted one or more times with substituents such as those listed above.

FIG. 1 is an illustration of a reaction apparatus 1. The reaction apparatus 1 may be suitable for reactive distillation and may be described as a reactive distillation system. The reaction apparatus 1 may comprise a drive sheave 10 or gear which may be configured to operably interface with a motor and/or gear or pulley system to rotate the drive sheave 10 and components attached thereto around an axis of rotation 5. The drive sheave 10 may rotate clockwise, counter-clockwise, or a combination of these, such as oscillating back and forth between clockwise and counter-clockwise rotations. The apparatus 1 may comprise a drive shaft 20 operably connected to the drive sheave 10, where the drive shaft 20 may rotate in conjunction with the rotation of the drive sheave 10. The drive shaft 20 may be an integral part of the drive sheave 10, such as where the drive sheave 10 and drive shaft 20 form a single piece of material. The drive sheave 10 and drive shaft 20 may be separate pieces which are operably connected to each other.

The drive shaft 20 may comprise a material or a combination of materials configured to provide stiffness and strength to the drive shaft 20, where the stiffness and strength may be sufficient to overcome cantilever action and fatigue to the drive shaft 20 during rotation under load. The drive shaft may comprise metal, plastic, filled plastic such as glass filled plastic, carbon graphite, or a combination of these. The drive shaft material may be selected to provide the appropriate corrosion resistance to the environment of the reaction in the reaction apparatus 1, such as strongly acid, basic, oxidizing, reducing, etc. For example, the drive shaft 20 may comprise outer covering or sheath comprising a polymer and a stainless steel core, where the core may provide stiffness and strength to the polymer. In one embodiment, the drive shaft 20 may be comprised of stainless steel, where the stainless steel may provide both resistance to corrosion by acids such as HCl, and stiffness and strength. The drive shaft 20 surface may be coated or encapsulated with an appropriate material configured to compatiblize the drive shaft 20 wetted surfaces. Such appropriate materials may include fluorinated polyolefins, such as poly(tetrafluoroethylene) (PTFE), poly(vinylidene fluoride) (PVDF), or perfluoroelastomers (FFKM), for example.

The reaction apparatus 1 may comprise a bearing housing 30 through which the drive shaft 20 may be operably disposed. The bearing housing 30 may be configured to hold the drive shaft 20 in an upright position while allowing rotation of the drive shaft 20 about its axis. The bearing housing 30 may be configured to provide an air-tight seal around the drive shaft 20 such that a vacuum may be maintained within the reaction apparatus 1. The bearing housing 30 may comprise appropriate seals to provide both an air-tight seal within the reaction apparatus 1 and resistance to corrosion. For example, the bearing housing 30 may comprise packing and lip seals comprising PTFE or other suitable materials. The bearing housing 30 may comprise bearings such as roller bearings or ball bearings to allow for smooth rotation of the drive shaft 20 with a reduced level of resistance. The bearing housing may comprise a single piece design or may comprise multiple pieces fitted and sealed together in a manner which provides the required support and rotation for the drive shaft 20 while maintaining a vacuum inside the reaction apparatus 1. The bearing housing 30 may comprise a material having sufficient strength to support the forces associated with the rotation of the drive shaft 20. The bearing housing 30 may comprise a material or combination of materials having corrosion resistance to solvents, acids, and/or bases which may be present in the reaction apparatus 1. For example, the bearing housing 30 may comprise a polymer such as PTFE. The bearing housing 30 may comprise a filled polymer which may provide additional strength, such as glass filled PTFE. In one embodiment, the bearing housing 30 may comprise 25% glass-filled PTFE.

The reaction apparatus 1 may comprise a clamp ring 40 through which the drive shaft 20 and bearing housing 30 may be passed. The clamp ring 40, in combination with a flange clamp 130, may be configured to secure or mount the reactor body 70 of the reaction apparatus 1 to a bulkhead 120 or equivalent device which may serve to support the reaction apparatus 1. The clamp ring 40 and flange clamp 130 may be secured or fastened with fasteners 230 such as screws, bolts, spring clamps, or other fastening devices known in the art. The clamp ring 40 and flange clamp 130 may comprise materials resistant to strong bases, solvents, acids, or a combination of these. In one embodiment, the clamp ring 40 and flange clamp 130 comprise stainless steel.

The reaction apparatus 1 may comprise an upper seal 50 disposed on one end of the reactor body 70. The seal may be disposed between a surface on the end of the reactor body 70 and a mating surface on a seal plate 220 clamped to the bulkhead 120. The surface of the end of the reactor body and the mating surface of the seal plate 220 may comprise a contour or configuration to accommodate the upper seal 50, such as a groove which seats the upper seal 50 and allows for an air-tight seal. The seal plate may comprise a threaded configuration which allows it to thread into a corresponding thread configuration in an end of the reactor body. The seal may be configured to seal the end of the reaction apparatus 1 to allow a vacuum to be established inside the reaction apparatus 1 and/or to introduce inert gasses into the reaction apparatus. The upper seal 50 may comprise an o-ring, v-ring, a gasket, or the like. The upper seal may comprise an elastomer such as a fluorinated elastomer, such as VITON. The upper seal may comprise a material, such as PTFE, which is resistant to acids such as HCl.

The reactor body 70 may be essentially cylindrical and comprise a hollow interior 73. The reactor body 70 may comprise a plurality of ports and/or openings, such as through which reactant materials may introduced into the hollow interior 73, product materials may be removed from the hollow interior, coolant lines may enter and exit, etc. For example, the reactor body 70 may comprise at least one feed port 140, where reactants may be introduced such as through a metering device (such as a metering pump, etc.) configured to measure and dispense reactants of predetermined amounts or at predetermine rates, where the port may be configured to accept reactants into the reactor body at a rate greater than about 1.5 liters/hour (l/h). The reactor body 70 may comprise at least one vapor out port 60, where reaction products may be removed in the vapor phase from the reaction apparatus 1 and isolated, such as through a condenser. The reaction apparatus may thus comprise multiple feed ports and/or out ports as deemed appropriate by a user.

The reactor body 70 may comprise a corrosion resistant material which is resistant to corrosion by strong acids, strong bases, solvents, or a combination of these. For example, the reactor body 70 may comprise an acid resistant material or combination of materials, such as glass or glass-lined steel, where the materials may be resistant to strong acids such as HCl. The exact choice of corrosion resistant material may depend on the reaction performed by a user in the reaction apparatus 1.

The reactor body 70 may further comprise an end cap 240 configured to removably cover and seal an open end of the reactor body 70. The end cap 240 may be disposed on an end of the reactor body 70 opposing an end of the reactor body 70 having the upper seal 50. For example, the end cap 240 may be disposed on the bottom end of the reactor body 70. The end cap 240 may be sealed to the end of the reactor body 70 using a lower seal 190, where the lower seal 190 may have properties and configurations such as those described above for the upper seal 220, such as resistance to acids, bases and solvents. The end cap 240 in combination with the lower seal 190 may provide an air-tight seal to allow evacuation of the reactor body 70. The lower seal 190 and upper seal 220 may be configured such that a vacuum or partial vacuum may be maintained within the reactor body 70, such as a pressure between about 266.6 pascal (Pa) (about 2 Torr) and about 101.3 kilopascals (kPa) (about 760 Torr). The end cap 240 and a corresponding mating end of the reactor body 70 may each comprise surfaces for retaining the lower seal 190, such as described above regarding the upper seal 50. The end cap 240 and lower seal 190 may be secured to the corresponding mating end of the reactor body 70 using a clamp assembly 90 configured to retain and hold the end cap 240 and the lower seal 90 to the corresponding end of the reactor body 70. The clamp assembly 90 may comprise, for example a clamp ring in combination with a flange clamp such as is described above for the seal plate 220.

The end cap 240 may comprise materials such as those described above for the reactor body 70. The end cap 240 may comprise a plurality of openings, such as at least one product out port 200 through which reaction products, such as liquid products may be removed from the reaction apparatus 1. The end cap 240 may comprise at least one condensate out port 105 through which condensed reaction products, such as HCl, may be removed from the reaction apparatus 1.

The reaction apparatus 1 may comprise an internal condenser 180, disposed inside of and extending through a portion of the hollow interior 73 of the reactor body 70 and configured to provide a condensing surface for materials within the hollow interior 73 of the reactor body 70. The internal condenser 180 may be reversibly attached to the end cap 240 or may be integral with the end cap 240. The internal condenser 180 may comprise an inlet port 110 through which coolant may be introduced and an outlet port 210 through which coolant may exit, where the coolant is isolated from the interior of the reactor body 70. The internal condenser 180 may be configured to use different coolants as needed to allow a range of temperatures as may be required for condensing products within the reactor body. The internal condenser 180 may comprise a material or a combination of materials resistant to corrosion by strong acids, strong bases, solvents, etc., such as those described above for the reactor body 70.

The reaction apparatus 1 may comprise at least one temperature regulating device 80 disposed on an outer surface of the reactor body. The temperature regulating device may be configured to regulate the temperature of the reactor body and/or reaction materials inside the reactor body 70 within a temperature range of from about 0° C. to about 250° C., such as between about 70° C. and about 90° C. The at least one temperature regulating device 80 may be capable of heating the reactor body 70 and may comprise a heating band, a heating blanket or jacket, the like, or a combination of these. The at least one temperature regulating device 80 may comprise appropriate thermostatic controls and/or thermocouples configured to measure and regulate the temperature of the at least one temperature regulating device 80 and the reactor body 70. In one embodiment, the at least one temperature regulating device may comprise a plurality of electric heating elements (such as bands) where each heating elements of the plurality of heating elements 80 may be individually configured with appropriate thermostatic controls to allow independently heating each area covered by each heating band to a specific temperature. For example, heating bands at the lower end of the reactor body 70 may be at higher temperatures than heating bands at the higher end of the reactor body 70, thus providing a temperature gradient along the length of the reactor body 70.

The reaction apparatus may comprise a rotor 150 disposed within the interior of the reactor body 70 and operably attached to the drive shaft 20 such that rotation of the drive shaft 20 about the drive shaft axis 5 results in rotating the rotor

150. The rotor 150 may comprise an axis of rotation collinear with the axis of rotation 5 of the drive shaft 20. The rotor 150 may be configured to rotate and mix reaction components (reactants, products, solvents, etc.) within the reaction body 70 during a reaction. The drive sheave 10, drive shaft 20, and rotor 150 may be configured such that the rotor may be rotated at a speed between about 50 rpm (revolutions/minute) and about 400 rpm. The rotor 150 may further comprise at least one vent 170 or slot operably connected to the rotor 150 or integral with the rotor 150, where the at least one vent 170 may be configured to allow flow of materials through the rotor 150 and aid in mixing. The at least one vent 170 may be angled to minimize radiant heat transfer profiles from an inner wall of the reactor body 70 towards the center of the interior of the reactor body 70. The rotor 150 may be configured to hold and may comprise at least one free-floating wiper element 160, where the wiper element may be disposed between the rotor and an inner wall of the reactor body. The wiper element 160 may be configured to wipe or otherwise remove solid materials from an inside wall of the reactor body 70, where the solid materials may form as precipitate from a reaction, for example. The rotor may be comprise a single piece of material or may comprise more than one piece. A single piece design may provide a balanced rotation of the rotor 150. A multiple piece design may provide reduced cost for manufacture and flexibility in design variation. The rotor 150, vents 170, and wiper 160 may comprise corrosion resistant materials such as those described above. For example, the rotor may comprise 25% glass-filled PTFE.

Figure 2:
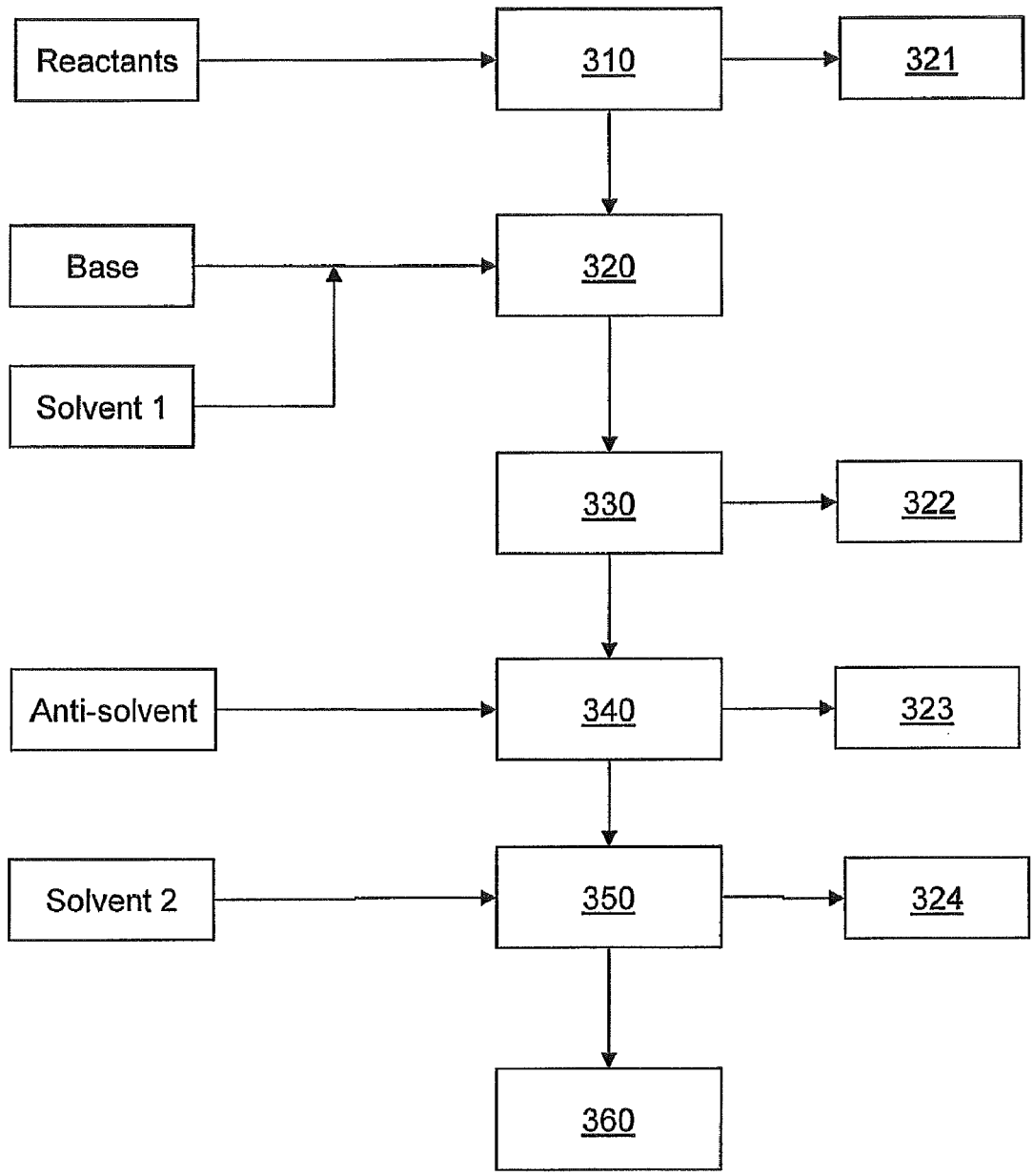
FIG. 2 is an illustration of a flow chart comprising a method for continuous production of metal alkoxides, in accordance with embodiments of the present invention.

FIG. 2 is an illustration of a flow chart comprising a method for continuous production of metal alkoxides, such as by reaction of a metal compound and an alcohol. Step 310 comprises a reactive distillation stage in which amounts of reactants are continuously introduced, injected, or otherwise placed into a reaction-distillation zone, such as by introducing an aqueous solution of a metal compound and alcohol into a reaction-distillation zone of a reaction apparatus, such as the reaction apparatus 1 described above and illustrated in FIG. 1. The metal to alcohol ratio may be controlled by independently controlling the amounts introduced into the reaction-distillation zone The ratio of metal to alcohol is generally in the range of from about 1 to 1 to about 1 to 6, for example 1 to 2. The metal compound may be contacted with the alcohol under conditions such as those described herein, such that the metal compound and the alcohol react to form a metal alkoxide compound.

The term reaction-distillation zone as used herein may comprise an area or volume within a reaction apparatus where a chemical reaction is occurring simultaneously with the distillation and condensation of reactants, solvents, and products within the reaction apparatus. The reaction-distillation zone may comprise a distinct vapor phase where one or more reaction components (reactants, products, solvents, etc.) may be present in a vapor phase, and a distinct liquid phase where one or more reaction components may be present in the liquid phase (such as dissolved in solution or present as precipitated solid within the liquid, for example). Conditions within the reaction apparatus may be maintained such that distinct vapor and liquid phases exist simultaneously, such as by maintaining heating of the reactor body and reaction components therein.

Amounts of the reactants may be continuously introduced into the reaction apparatus at a rate of about 1.5 L/hr or higher (such as through feed port 140 in FIG. 1) during the reaction as reaction products are simultaneously removed or withdrawn from the reaction apparatus. Reaction products may be removed from the vapor phase of the reaction-distillation zone, the liquid phase of the reaction-distillation zone, or a combination of these. A reaction charge (such as an aqueous solution of metal compound and alcohol reactants) may be introduced into the reaction-distillation zone through a first feed port of the reaction apparatus, while individual reactants, such as alcohol, may be introduced through a second feed port, such as a feed port located near the top of the reaction zone.

The metal compound may comprise a metal salt (such as a metal halide), a metal hydroxide, a metal oxide, a metal alkoxide, or a combination thereof. For example, the metal compound may comprise titanium oxychloride, $TiOCl_2$. Halides of these metals may include fluorides, chlorides, bromides, and iodides. The metal of the metal compound may comprise one or more transition metals. Examples of metals within the scope of metal compounds as used herein include titanium, vanadium, chromium, manganese, iron, cobalt, nickel, copper, zinc, zirconium, niobium, molybdenum, ruthenium, rhodium, palladium, silver, hafnium, tantalum, tungsten, rhenium, osmium, iridium, platinum, gold, and elements of the lanthanide series (such as cesium, samarium, gadolinium, dysprosium, erbium, neodymium, etc.). The metal compound may comprise one or more of the metals described above. The metal may comprise a bivalent, trivalent, tetravalent, pentavalent, or hexavalent metal.

It is understood that certain metalloid compounds (such as metalloid salts, oxides, hydroxides, alkoxides, etc.) may possess properties which permit them to react as the metal compounds described above to form alkoxides through reactions with alcohols. For example, metalloids of the IUPAC (International Union of Pure and Applied Chemistry) periodic groups 13 through 16, such as boron and/or aluminum, are intended to be included within the scope of the present disclosure as compounds which may react as the metal compounds described herein. As used in this application, the term metal may refer to a metalloid and vice versa.

The alcohol may comprise any of $C_1$ to $C_{20}$ monohydric alcohols or polyhydric alcohols (polyols) having two or more OH groups which are capable of reacting with the metal compound. The alcohol may comprise an aromatic alcohol or an aliphatic alcohol. The alcohol may comprise, but is not limited to, ethylene glycol, glycerol, methoxypropanol, diethyleneglycol monomethylether, diethyleneglycol monobutylether, erythritol, sorbitol, a sugar, a starch, or the like.

Suitable alcohols for use in the synthesis of flame retardant metal alkoxide additives and compositions include, but are not limited to, alcohols of the general formula:

wherein R is an alkyl group (including linear, branched, saturated, unsaturated, cyclic, and substituted alkyl groups, and wherein hetero atoms, such as oxygen, nitrogen, sulfur, silicon, phosphorus, and the like can be present in the alkyl group), typically with from about 2 to about 30 carbon atoms, preferably with from about 2 to about 20 carbon atoms, and more preferably with from about 2 to about 10 carbon atoms, although the number of carbon atoms can be outside of these ranges; an aryl group (including substituted aryl groups), typically with from about 6 to about 30 carbon atoms, preferably with from about 6 to about 20 carbon atoms, and more preferably with from about 6 to about 12 carbon atoms, although the number of carbon atoms can be outside of these ranges; an arylalkyl group (including substituted arylalkyl groups), typically with from about 7 to about 30 carbon atoms, preferably with from about 7 to about 20 carbon atoms, and more preferably with from about 7 to about 14 carbon atoms, although the number of carbon atoms can be outside of these ranges, such as benzyl or the like; an alkylaryl group (including substituted alkylaryl groups), typically with from about 7 to about 30 carbon atoms, preferably with from about 7 to about 20 carbon atoms, and more preferably with from about 7 to about 12 carbon atoms, although the number of carbon atoms can be outside of these ranges; an alkoxy group (including substituted alkoxy groups, and wherein hetero atoms, such as oxygen, nitrogen, sulfur, silicon, phosphorus, and the like can be present in the alkoxy group), typically with from about 2 to about 30 carbon atoms, preferably with from about 2 to about 20 carbon atoms, and more preferably with from about 2 to about 12 carbon atoms, although the number of carbon atoms can be outside of these ranges; a polyalkyleneoxy group (including substituted polyalkyleneoxy groups), such as polyethyleneoxy groups, polypropyleneoxy groups, polybutyleneoxy groups, and the like, typically with from about 3 to about 60 repeat alkyleneoxy units, preferably with from about 3 to about 30 repeat alkyleneoxy units, and more preferably with from about 3 to about 20 repeat alkyleneoxy units, although the number of repeat alkyleneoxy units can be outside of these ranges, wherein the substituents on the substituted alkyl, aryl, arylalkyl, alkylaryl, alkoxy, and polyalkyleneoxy groups can be (but are not limited to) hydroxy groups, amine groups, pyridine groups, ether groups, ester groups, amide groups, carbonyl groups, mixtures thereof, and the like, wherein two or more substituents can be joined together to form a ring.

In some embodiments, the alcohol comprises a polyol having a substituted alkyl group, a substituted cycloalkyl group, a substituted cycloalkylalkyl group, a substituted heterocyclyl group, a substituted heterocyclylalkyl group, or combination thereof.

Suitable alcohols for use in the synthesis of flame retardant cyclic metal alkoxide additives and compositions include, but are not limited to, polyols of the general formula:

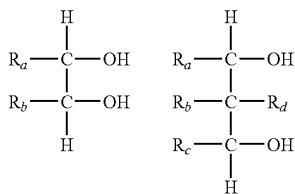

In some embodiments, the alcohol comprises an alkanolamine. Suitable alkanolamines for use in the synthesis of flame retardant metal alkoxide additives and compositions include, but are not limited to, alkanolamines of the general formula:

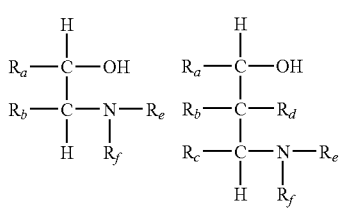

wherein Ra, Rb, Rc, Rd, Re, and Rf each, independently of the others, can be a hydrogen atom, an alkyl group (including linear, branched, saturated, unsaturated, cyclic, and substituted alkyl groups, and wherein hetero atoms, such as oxygen, nitrogen, sulfur, silicon, phosphorus, and the like can be present in the alkyl group), typically with from 1 to about 22 carbon atoms, preferably with from 1 to about 12 carbon atoms, and more preferably with from 1 to about 6 carbon atoms, although the number of carbon atoms can be outside of these ranges; an aryl group (including substituted aryl groups), typically with from about 6 to about 22 carbon atoms, preferably with from about 6 to about 15 carbon atoms, and more preferably with from about 6 to about 10 carbon atoms, although the number of carbon atoms can be outside of these ranges; an arylalkyl group (including substituted arylalkyl groups), typically with from about 7 to about 22 carbon atoms, preferably with from about 7 to about 15 carbon atoms, and more preferably with from about 7 to about 12 carbon atoms, although the number of carbon atoms can be outside of these ranges, such as benzyl or the like; an alkylaryl group (including substituted alkylaryl groups), typically with from about 7 to about 22 carbon atoms, preferably with from about 7 to about 15 carbon atoms, and more preferably with from about 7 to about 12 carbon atoms, although the number of carbon atoms can be outside of these ranges; an alkoxy group (including substituted alkoxy groups, and wherein hetero atoms, such as oxygen, nitrogen, sulfur, silicon, phosphorus, and the like can be present in the alkoxy group), typically with from 1 to about 22 carbon atoms, preferably with from 1 to about 15 carbon atoms, and more preferably with from 1 to about 12 carbon atoms, although the number of carbon atoms can be outside of these ranges; a polyalkyleneoxy group (including substituted polyalkyleneoxy groups, and wherein hetero atoms, such as oxygen, nitrogen, sulfur, silicon, phosphorus, and the like can be present in the polyalkyleneoxy group), such as polyethyleneoxy groups, polypropyleneoxy groups, polybutyleneoxy groups, and the like, typically with from about 3 to about 60 repeat alkyleneoxy units, preferably with from about 3 to about 30 repeat alkyleneoxy units, and more preferably with from about 3 to about 10 repeat alkyleneoxy units, although the number of repeat alkyleneoxy units can be outside of these ranges; a hydroxy group, an amine group, a pyridine group, an ether group, an ester group, an amide group, a carbonyl group, mixtures thereof, and the like, wherein Ra, Rb, Rc, Rd, Re, and/or Rf can be joined together to form a ring, and wherein the substituents on the substituted alkyl, aryl, arylalkyl, alkylaryl, alkoxy, and polyalkyleneoxy groups can be (but are not limited to) hydroxy groups, amine groups, pyridine groups, ether groups, ester groups, amide groups, carbonyl groups, mixtures thereof, and the like, wherein two or more substituents can be joined together to form a ring. For example, when Ra, Rb, Rc, Rd, Re, and/or Rf are themselves or are substituted with ester groups, these groups can be of the formul:

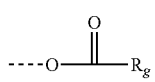

wherein Rg is defined as Ra through Rf above. Examples of materials within these general formulae include:

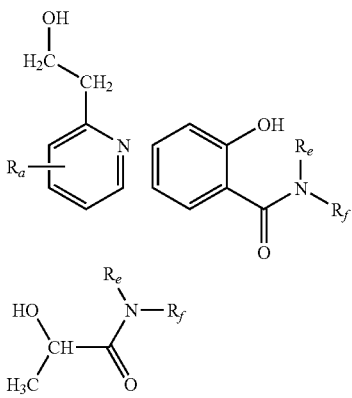

and the like.

In particular, suitable alcohols, polyols and alkanolamines for use in the synthesis of flame retardant metal alkoxide additives and compositions include, but are not limited to, glycerol, sorbitol, xylitol, mannitol, glyceroloxyglycerol, 1,3-propanediol, triethylene glycol monomethyl ether, glycerin laurate, di-N-butylethanolamine, beta-branched alcohols, salicylamide, lactamide, and/or a combination thereof.

In some embodiments, the alcohol may have a boiling point higher than 100° C. In some embodiments, the alcohol may have a boiling point higher than 100° C. where the alcohol does not form an azeotrope with water. In some embodiments, the alcohol may have a boiling point higher than 100° C. where the alcohol does not form a ternary azeotrope with water and HCl. The alcohol as used herein may have a "high boiling point", where the phrase "high boiling point" includes materials having a boiling point in excess of 50° C., 60° C., 70° C., 80° C., 90° C., 100° C., 120° C., 140° C., 160° C., 180° C., or 200° C. at atmospheric pressure. In some embodiments, a high boiling point material has a boiling point from about 200° C. to about 600° C. at atmospheric pressure.

The reactions of the metal compounds and the alcohols may include reactions described by the following:

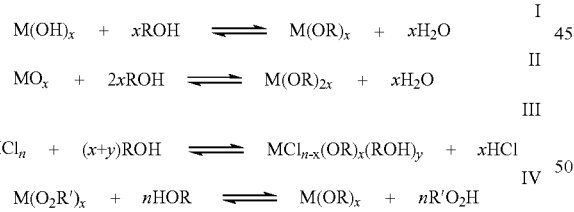

where x and y are integers from 1 to 4, n is an integer from 1 to 8, and M is a metal such as those described above. R and R' may be each independently comprise a hydrogen, substituted alkyl group, unsubstituted alkyl group, substituted aryl group, unsubstituted aryl group, or a combination of these. For example, R and R' may each independently be substituted or unsubstituted ethyl, propyl, butyl groups, etc.

The reactions as described herein of the metal compounds above with alcohols, where the alcohols are polyols, may be described by the following:

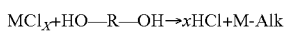

where x is an integer from 1 to about 8. The group R may comprise a group as described above which does not include a hydroxyl group, such as where the group HO—R—OH comprises ethylene glycol, propylene glycol, etc. In some embodiments the group R may comprise at least one hydroxyl group, such as where HO—R—OH comprises glycerol, erythritol, sorbitol, etc.

The compound M-Alk in reaction V may comprise a metal alkoxide where the metal alkoxide may be described by one of the following:

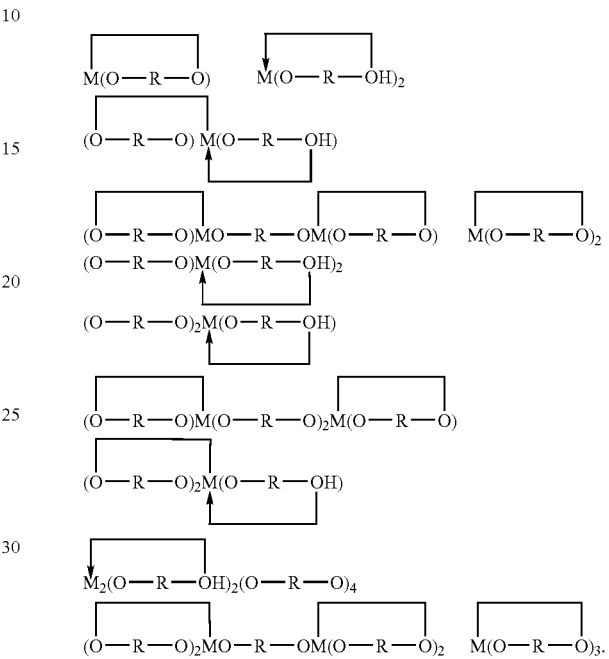

In some embodiments, the metal compound reactant may comprise a metal alkoxide, where the metal alkoxide reactant may react with a polyol to form a different metal alkoxide product, such as those having structures represented by:

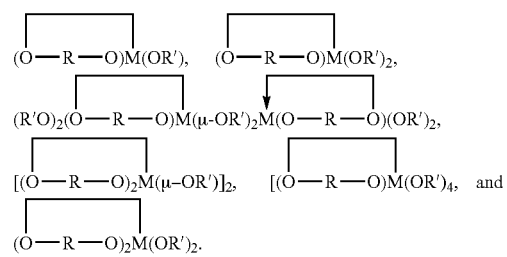

The metal alkoxide products as described herein may comprise a complex, a cluster complex, a mixture of isomers, a nano-dimensional metal alkoxide material, or a combination thereof. Nano-dimensional metal alkoxide material may comprise nanoparticles of metal alkoxide product, where the nanoparticles may be produced by controlled hydrolysis. The nanoparticles may be sintered following formation. Nanoparticles thus produced may used as components of organic solutions, suspensions, and composites.

Amounts of reaction products may be continuously withdrawn from the reaction-distillation zone while simultaneously both introducing amounts of reactants and contacting amounts of reactants in the reaction-distillation zone, thus creating a continuous reaction production process. Reaction products may be continuously withdrawn from the reaction-distillation zone, such as withdrawing liquid from the liquid phase containing dissolved reaction products, such as metal alkoxide compound, alcohol, acid by-product, etc. Reaction products, such as water and acid, may be continuously withdrawn from the reaction-distillation zone, such as from the vapor phase. The metal compound may thus be reacting with the alcohol while, simultaneously, removing products from the reaction-distillation zone, such as removing acid products from the vapor phase. During the reaction, the reaction apparatus may thus simultaneously comprise a stream of reactants entering the reaction-distillation zone, a stream of products exiting the vapor phase of the reaction-distillation zone, and a stream of products existing the liquid phase of the reaction-distillation zone.

Reaction products of the above reactions may comprise an inorganic acid, an organic acid, carbon dioxide, sulfur oxides, nitrogen oxides, an organic alcohol, or a combination thereof. Water vapor removed from the vapor phase may be captured through condensation and returned to the reaction-distillation zone. Reaction products removed from the liquid phase may undergo neutralization to neutralize acid residue and may undergo washing to remove excess alcohol and to isolate metal alkoxide product (vide infra).

It has been found that the metal alkoxide reaction product of Equation I above, wherein M is a group 13 metal or metalloid, or commonly referred to as a group 13 ester, is useful as a flame retardant and/or flame retardant additive.

Suitable group 13 metal alkoxides useful as flame retardants and/or flame retardant additives include, but are not limited to, group 13 metal alkoxides of the general formula:

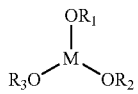

wherein M is boron, aluminum, and/or mixtures thereof and $R_1$, $R_2$, and $R_3$ each, independently of the others, is a hydrogen group, an alkyl group (including linear, branched, saturated, unsaturated, cyclic, and substituted alkyl groups, and wherein hetero atoms, such as oxygen, nitrogen, sulfur, silicon, phosphorus, and the like can be present in the alkyl group), typically with from about 2 to about 30 carbon atoms, preferably with from about 2 to about 20 carbon atoms, and more preferably with from about 2 to about 12 carbon atoms, although the number of carbon atoms can be outside of these ranges; an aryl group (including substituted aryl groups), typically with from about 6 to about 24 carbon atoms, preferably with from about 6 to about 15 carbon atoms, and more preferably with from about 6 to about 12 carbon atoms, although the number of carbon atoms can be outside of these ranges; an arylalkyl group (including substituted arylalkyl groups), typically with from about 7 to about 25 carbon atoms, preferably with from about 7 to about 16 carbon atoms, and more preferably with from about 7 to about 13 carbon atoms, although the number of carbon atoms can be outside of these ranges, such as benzyl or the like; an alkylaryl group (including substituted alkylaryl groups), typically with from about 7 to about 25 carbon atoms, preferably with from about 7 to about 16 carbon atoms, and more preferably with from about 7 to about 13 carbon atoms, although the number of carbon atoms can be outside of these ranges; an alkoxy group (including substituted alkoxy groups, and wherein hetero atoms, such as oxygen, nitrogen, sulfur, silicon, phosphorus, and the like can be present in the alkoxy group), typically with from about 2 to about 30 carbon atoms, preferably with from about 2 to about 20 carbon atoms, and more preferably with from about 2 to about 12 carbon atoms, although the number of carbon atoms can be outside of these ranges, a polyalkyleneoxy group (including substituted polyalkyleneoxy groups), such as polyethyleneoxy groups, polypropyleneoxy groups, polybutyleneoxy groups, and the like, typically with from about 2 to about 60 repeat alkyleneoxy units, preferably with from about 2 to about 30 repeat alkyleneoxy units, and more preferably with from about 2 to about 20 repeat alkyleneoxy units, although the number of repeat alkyleneoxy units can be outside of these ranges, wherein the substituents on the substituted alkyl, aryl, arylalkyl, alkylaryl, alkoxy, and polyalkyleneoxy groups can be (but are not limited to) hydroxy groups, amine groups, pyridine groups, ether groups, ester groups, amide groups, carbonyl groups, mixtures thereof, and the like, wherein two or more substituents can be joined together to form a ring, and wherein $R_1$, $R_2$, and/or $R_3$ can be joined together to form an aliphatic or aromatic ring, and those of the general formulae:

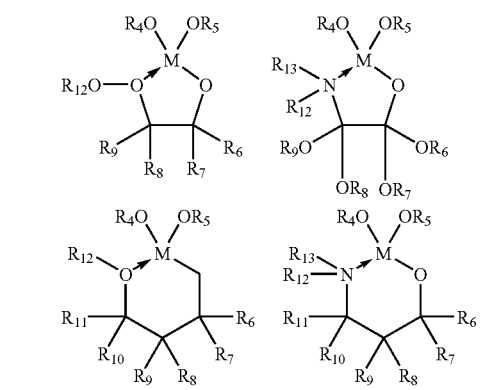

wherein $R_4$ and $R_5$ each, independently of the other, is an alkyl group (including linear, branched, saturated, unsaturated, cyclic, and substituted alkyl groups, and wherein hetero atoms, such as oxygen, nitrogen, sulfur, silicon, phosphorus, and the like can be present in the alkyl group), typically with from about 2 to about 30 carbon atoms, preferably with from about 2 to about 20 carbon atoms, and more preferably with from about 2 to about 12 carbon atoms, although the number of carbon atoms can be outside of these ranges; an aryl group (including substituted aryl groups), typically with from about 6 to about 24 carbon atoms, preferably with from about 6 to about 15 carbon atoms, and more preferably with from about 6 to about 12 carbon atoms, although the number of carbon atoms can be outside of these ranges; an arylalkyl group (including substituted arylalkyl groups), typically with from about 7 to about 25 carbon atoms, preferably with from about 7 to about 16 carbon atoms, and more preferably with from about 7 to about 13 carbon atoms, although the number of carbon atoms can be outside of these ranges, such as benzyl or the like; an alkylaryl group (including substituted alkylaryl groups), typically with from about 7 to about 25 carbon atoms, preferably with from about 7 to about 16 carbon atoms, and more preferably with from about 7 to about 13 carbon atoms, although the number of carbon atoms can be outside of these ranges; an alkoxy group (including substituted alkoxy groups, and wherein hetero atoms, such as oxygen, nitrogen, sulfur, silicon, phosphorus, and the like can be present in the alkoxy group), typically with from about 2 to about 30 carbon atoms, preferably with from about 2 to about 20 carbon atoms, and more preferably with from about 2 to about 12 carbon atoms, although the number of carbon atoms can be outside of these ranges; a polyalkyleneoxy group (including substituted polyalkyleneoxy groups, and wherein hetero atoms, such as oxygen, nitrogen, sulfur, silicon, phosphorus, and the like can be present in the polyalkyleneoxy group), such as polyethyleneoxy groups, polypropyleneoxy groups, polybutyleneoxy groups, and the like, typically with from about 3 to about 60 repeat alkyleneoxy units, preferably with from about 3 to about 30 repeat alkyleneoxy units, and more preferably with from about 3 to about 20 repeat alkyleneoxy units, although the number of repeat alkyleneoxy units can be outside of these ranges, wherein $R_4$ and $R_5$ can be joined together to form a ring, $R_6$, $R_7$, $R_8$, $R_9$, $R_{10}$, and $R_{11}$ each, independently of the other, is a hydrogen atom, an alkyl group (including linear, branched, saturated, unsaturated, cyclic, and substituted alkyl groups, and wherein hetero atoms, such as oxygen, nitrogen, sulfur, silicon, phosphorus, and the like can be present in the alkyl group), typically with from 1 to about 22 carbon atoms, preferably with from 1 to about 12 carbon atoms, and more preferably with from 1 to about 6 carbon atoms, although the number of carbon atoms can be outside of these ranges, an aryl group (including substituted aryl groups), typically with from about 6 to about 22 carbon atoms, preferably with from about 6 to about 15 carbon atoms, and more preferably with from about 6 to about 10 carbon atoms, although the number of carbon atoms can be outside of these ranges; an arylalkyl group (including substituted arylalkyl groups), typically with from about 7 to about 22 carbon atoms, preferably with from about 7 to about 15 carbon atoms, and more preferably with from about 7 to about 12 carbon atoms, although the number of carbon atoms can be outside of these ranges, such as benzyl or the like, an alkylaryl group (including substituted alkylaryl groups), typically with from about 7 to about 22 carbon atoms, preferably with from about 7 to about 15 carbon atoms, and more preferably with from about 7 to about 12 carbon atoms, although the number of carbon atoms can be outside of these ranges, an alkoxy group (including substituted alkoxy groups, and wherein hetero atoms, such as oxygen, nitrogen, sulfur, silicon, phosphorus, and the like can be present in the alkoxy group), typically with from 1 to about 22 carbon atoms, preferably with from 1 to about 12 carbon atoms, and more preferably with from 1 to about 7 carbon atoms, although the number of carbon atoms can be outside of these ranges, a polyalkyleneoxy group (including substituted polyalkyleneoxy groups, and wherein hetero atoms, such as oxygen, nitrogen, sulfur, silicon, phosphorus, and the like can be present in the polyalkyleneoxy group), such as polyethyleneoxy groups, polypropyleneoxy groups, polybutyleneoxy groups, and the like, typically with from about 3 to about 30 repeat alkyleneoxy units, preferably with from about 3 to about 20 repeat alkyleneoxy units, and more preferably with from about 3 to about 10 repeat alkyleneoxy units, although the number of repeat alkyleneoxy units can be outside of these ranges, a hydroxy group, an amine group, a pyridine group, an ether group, an ester group, an amide group, a carbonyl group, mixtures thereof, and the like, wherein one or more of $R_6$, $R_7$, $R_8$, $R_9$, $R_{10}$, and $R_{11}$ can be absent if a ring carbon atom has a double bond or a triple bond to another R group or to another ring carbon atom (for example, if $R_6$ is a=O carbonyl group, $R_7$ would be absent), and $R_{12}$ and $R_{13}$ each, independently of the other, is a hydrogen atom, an alkyl group (including linear, branched, saturated, unsaturated, cyclic, and substituted alkyl groups, and wherein hetero atoms, such as oxygen, nitrogen, sulfur, silicon, phosphorus, and the like can be present in the alkyl group), typically with from 1 to about 30 carbon atoms, preferably with from 1 to about 20 carbon atoms, and more preferably with from 1 to about 12 carbon atoms, although the number of carbon atoms can be outside of these ranges, an aryl group (including substituted aryl groups), typically with from about 6 to about 24 carbon atoms, preferably with from about 6 to about 15 carbon atoms, and more preferably with from about 6 to about 12 carbon atoms, although the number of carbon atoms can be outside of these ranges, an arylalkyl group (including substituted arylalkyl groups), typically with from about 7 to about 25 carbon atoms, preferably with from about 7 to about 16 carbon atoms, and more preferably with from about 7 to about 13 carbon atoms, although the number of carbon atoms can be outside of these ranges, such as benzyl or the like, an alkylaryl group (including substituted alkylaryl groups), typically with from about 7 to about 25 carbon atoms, preferably with from about 7 to about 16 carbon atoms, and more preferably with from about 7 to about 13 carbon atoms, although the number of carbon atoms can be outside of these ranges, an alkoxy group (including substituted alkoxy groups, and wherein hetero atoms, such as oxygen, nitrogen, sulfur, silicon, phosphorus, and the like can be present in the alkoxy group), typically with from 1 to about 30 carbon atoms, preferably with from 1 to about 20 carbon atoms, and more preferably with from 1 to about 12 carbon atoms, although the number of carbon atoms can be outside of these ranges, a polyalkyleneoxy group (including substituted polyalkyleneoxy groups, and wherein hetero atoms, such as oxygen, nitrogen, sulfur, silicon, phosphorus, and the like can be present in the polyalkyleneoxy group), such as polyethyleneoxy groups, polypropyleneoxy groups, polybutyleneoxy groups, and the like, typically with from about 2 to about 60 repeat alkyleneoxy units, preferably with from about 2 to about 30 repeat alkyleneoxy units, and more preferably with from about 2 to about 20 repeat alkyleneoxy units, although the number of repeat alkyleneoxy units can be outside of these ranges, wherein $R_6$, $R_7$, $R_8$, $R_9$, $R_{10}$, $R_{11}$, $R_{12}$, and/or $R_{13}$ can be joined together to form a ring, and wherein the substituents on the substituted alkyl, aryl, arylalkyl, alkylaryl, alkoxy, and polyalkyleneoxy groups can be (but are not limited to) hydroxy groups, amine groups, pyridine groups, ether groups, ester groups, amide groups, carbonyl groups, mixtures thereof, and the like, wherein two or more substituents can be joined together to form a ring.

In particular, suitable group 13 metal alkoxides useful as flame retardants and/or flame retardant additives include, but are not limited to, hydroxyaluminum glycerolate, of the formula and related isomers:

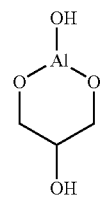

borate esters of glycerol, of the formulae:

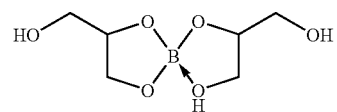

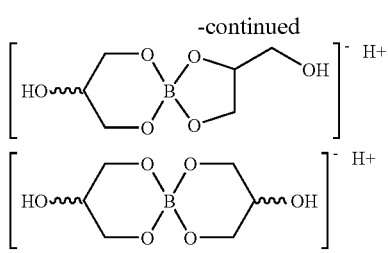

borate esters of sorbitol, of the formula and related isomers:

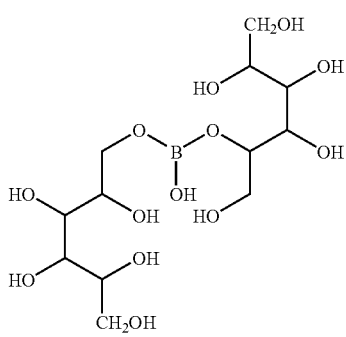

borate esters of erythritol, of the formula and related isomers:

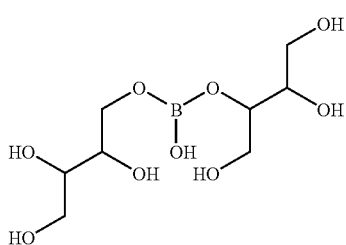

borate esters of pentaerythritol, of the formula and related isomers:

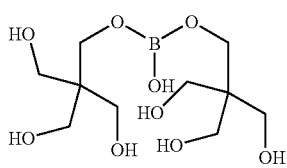

borate esters of xylitol, of the formula and related isomers:

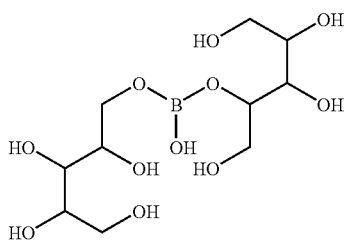

aluminate esters of glycerol, of the formula and related isomers:

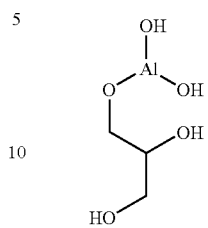

and/or mixtures thereof.

In addition to monomeric group 13 esters as set forth above, polymers and copolymers of group 13 esters have also been found to be useful as flame retardants and/or flame retardant additives. Copolymers of group 13 esters can be prepared by any known, such as by known methods for forming polyesters. For example, a monomeric group 13 ester compound having two primary or secondary alcohol groups thereon can be condensed with a diacid, such as those of the general formula HOOC—R—COOH, wherein R is an alkylene group, typically with from about 8 to about 82 carbon atoms, although the number of carbon atoms can be outside of this range, to extrude water and form a copolymer, as follows:

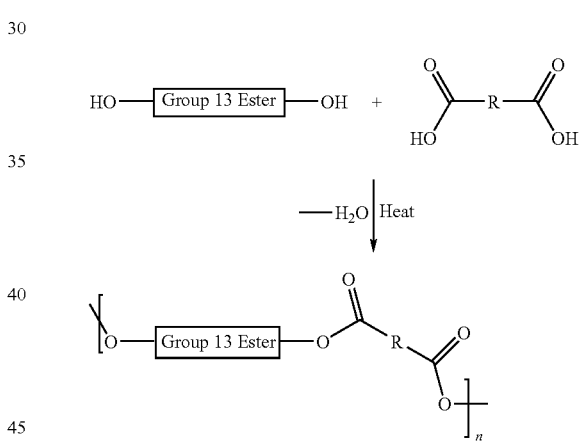

wherein n is an integer representing the number of repeat monomer units. Similarly, a group 13 ester having two acetyl groups thereon can be reacted with a diacid, such as those of the general formula HOOC—R—COOH, wherein R is an alkylene group, typically with from about 2 to about 22 carbon atoms, although the number of carbon atoms can be outside of this range, heating to extrude acetic acid and to form a copolymer, as follows:

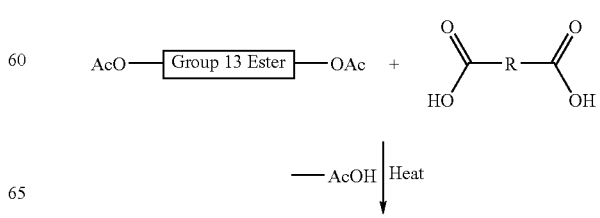

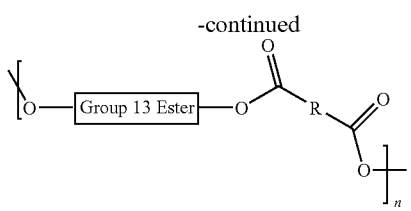

wherein n is an integer representing the number of repeat monomer units. Similarly, monomeric group 13 ester compound having two primary or secondary alcohol groups thereon can be reacted with a diester, such as those of the general formula $H_3COOC-R-COOCH_3$, wherein R is an alkylene group, typically with from about 2 to about 22 carbon atoms, although the number of carbon atoms can be outside of this range, heating to extrude methanol and to form a copolymer, as follows:

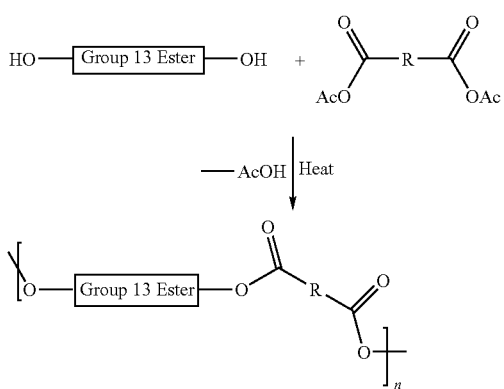

wherein n is an integer representing the number of repeat monomer units. In addition, a monomeric group 13 ester compound having two primary or secondary alcohol groups thereon can be reacted with a polyester to incorporate random monomer units of the group 13 ester into the polyester. For example, heating polyethylene terephthalate and diglycerol borate can result in extrusion of ethylene glycol and the formation of a random copolyester, as follows:

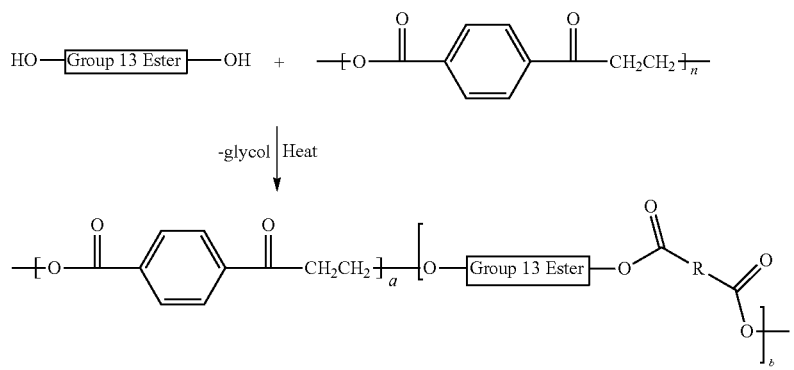

wherein a and b are integers representing the number of repeat monomer units. Polymeric borate esters are also disclosed in, for example, JP 11012524 A2, the disclosure of which is totally incorporated herein by reference. Borate ester compounds suitable for use as flame retardants and/or flame retardant additives include polymers having at least some repeat monomer units derived from monomeric borate esters.

Group 13 ester compounds can also be prepared by admixing boric acid with a primary or secondary alcohol or alkanolamine that will result in the desired ester compound and heating the mixture to remove water resulting from the reaction.

The group 13 ester is present in the flame retardant composition in an effective amount, typically at least about 0.001 percent by weight of the flame retardant composition, preferably at least about 5 percent by weight of the flame retardant composition, and more preferably at least about 10 percent by weight of the flame retardant composition, and typically no more than about 50 percent by weight of the flame retardant composition, preferably no more than about 40 percent by weight of the flame retardant composition, and more preferably no more than about 30 percent by weight of the flame retardant composition.

The flame retardant compositions of the present invention may be formulated with other additives and colorants which may improve or degrade the flame retardant properties of the present invention without falling outside the scope of the present invention. For example, it is well known that the addition of metal oxide ceramics (glass, pigments, and the like) improve the overall flame retardant properties of plastics and coatings owing to the formation of a char supporting surfaces and improved heat dissipation. Some synergistic improvements may arise as a result of maximizing the mode of action derived from the flame retardants of the present invention, without falling outside the scope of the present invention.

The flame retardant additives of the present invention may also be added to thermoplastics such as polypropylene, nylon, polystyrene, styrene-acrylonitrile copolymers, and butadiene-styrene-acrylonitrile terpolymers, or to thermoset polymers such as polyurethanes and epoxies, in order to make non-halogen fire retardant polymeric materials that, in a fire, will intumesce to provide better heat shielding and slow heat release rate. The percent by weight of the thermoplastic or thermoset material present can typically be at least about 50 percent by weight and no more than about 97 percent by weight, preferably not less than about 70 percent by weight, and more preferably no more than about 90 percent by weight of the material. The final flame retardant thermoplastic or thermoset polymer may take the form of thin film coatings, cast parts, injection molded parts, blow molded parts, extruded pellets, or any other common mode of commercial plastic/polymer processing without falling outside the scope of the present invention.

Hydrolytically stable group 13 esters can be used in the flame retardant compositions of the present invention without any stabilizing agent being present. If the borate ester is hydrolytically unstable, such that upon contact with water the borate ester decomposes to boric acid and the corresponding alcohol, the flame retardant compositions s of the present invention can further contain an amine stabilizing agent. Suitable amine stabilizing agents include, but are not limited to, amines of the general formula:

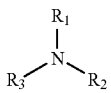

wherein R1, R2, and R3 each, independently of the others, can be hydrogen, an alkyl group (including linear, branched, saturated, unsaturated, cyclic, and substituted alkyl groups, and wherein hetero atoms, such as oxygen, nitrogen, sulfur, silicon, phosphorus, and the like can be present in the alkyl group), typically with from 1 to about 22 carbon atoms, preferably with from 1 to about 12 carbon atoms, and more preferably with from 1 to about 7 carbon atoms, although the number of carbon atoms can be outside of these ranges, an aryl group (including substituted aryl groups), typically with from about 6 to about 30 carbon atoms, preferably with from about 6 to about 15 carbon atoms, and more preferably with from about 6 to about 12 carbon atoms, although the number of carbon atoms can be outside of these ranges, an arylalkyl group (including substituted arylalkyl groups), typically with from about 7 to about 30 carbon atoms, preferably with from about 7 to about 15 carbon atoms, and more preferably with from about 7 to about 12 carbon atoms, although the number of carbon atoms can be outside of these ranges, such as benzyl or the like, an alkylaryl group (including substituted alkylaryl groups), typically with from about 7 to about 30 carbon atoms, preferably with from about 7 to about 15 carbon atoms, and more preferably with from about 7 to about 12 carbon atoms, although the number of carbon atoms can be outside of these ranges, an alkoxy group (including substituted alkoxy groups, and wherein hetero atoms, such as oxygen, nitrogen, sulfur, silicon, phosphorus, and the like can be present in the alkoxy group), typically with from 1 to about 22 carbon atoms, preferably with from 1 to about 12 carbon atoms, and more preferably with from 1 to about 7 carbon atoms, although the number of carbon atoms can be outside of these ranges, a polyalkyleneoxy group (including substituted polyalkyleneoxy groups), such as polyethyleneoxy groups, polypropyleneoxy groups, polybutyleneoxy groups, and the like, typically with from about 3 to about 60 repeat alkyleneoxy units, preferably with from about 3 to about 30 repeat alkyleneoxy units, and more preferably with from about 3 to about 20 repeat alkyleneoxy units, although the number of repeat alkyleneoxy units can be outside of these ranges, wherein two or more of R1, R2, and/or R3 can be joined together to form a ring, wherein the substituents on the substituted alkyl, aryl, arylalkyl, alkylaryl, alkoxy, and polyalkyleneoxy groups can be (but are not limited to) hydroxy groups, amine groups, pyridine groups, ether groups, ester groups, amide groups, carbonyl groups, mixtures thereof, and the like, wherein two or more substituents can be joined together to form a ring, and wherein at least one of R1, R2, and R3 is not hydrogen. In some instances tertiary amines are preferred, but secondary and primary amines can also be used.

In particular, suitable amine compounds include, but are not limited to, monoethanolamine, diethylamine, diethylamine diethanolamine, N,N-dibutylethanol amine, 2-hydroxyethylpyridine, 3-hydroxy-2-hydroxymethylpyridine, 2-hydroxymethylpyridine, 1-(2-hydroxyethylpyrrolidine), (4-(2-diethylamine, hydroxy ethyl)-1-piperazine propanesulfonic acid), triethanol amine, triethanolamine ethoxylate, and the like, as well as mixtures thereof.

When present, the amine is present in the flame retardant composition in any desired or effective amount, typically at least about 1 percent by weight of the flame retardant composition, preferably at least about 2 percent by weight of the flame retardant composition, and more preferably at least about 5 percent by weight of the flame retardant composition, and typically no more than about 10 percent by weight of the flame retardant composition.

Hydrolytically stable borate esters, for which no amine stabilizing agent is needed, include, but are not limited to, those having a nitrogen atom coordination bonded to the group 13 atom, such as those of the general formulae:

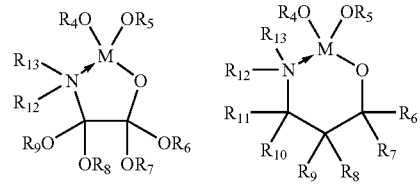

wherein the R groups are defined as indicated hereinabove. In a specific embodiment, the nitrogen atom coordination bonded to the group 13 atom has two other substituents (R12 and R13 for materials of the above formulae, for example) that are both alkyl groups with three or more carbon atoms, and preferably with four or more carbon atoms. Suitable examples of such group 13 esters include, but are not limited to:

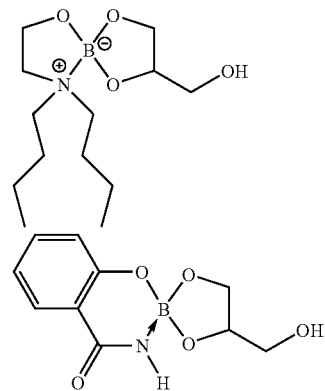

and the like. Hydrolytically stable borate esters also include those derived from beta-branched alcohols of the general formula:

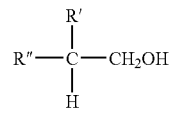

wherein R' and R" each, independently of the other, are alkyl groups (including linear, branched, saturated, unsaturated, cyclic, and substituted alkyl groups, and wherein hetero atoms, such as oxygen, nitrogen, sulfur, silicon, phosphorus, and the like can be present in the alkyl group), typically with from 1 to about 22 carbon atoms, preferably with from 1 to about 12 carbon atoms, and more preferably with from 1 to about 7 carbon atoms, although the number of carbon atoms can be outside of these ranges, aryl groups (including substituted aryl groups), typically with from about 6 to about 30 carbon atoms, preferably with from about 6 to about 15 carbon atoms, and more preferably with from about 6 to about 12 carbon atoms, although the number of carbon atoms can be outside of these ranges, arylalkyl groups (including substituted arylalkyl groups), typically with from about 7 to about 30 carbon atoms, preferably with from about 7 to about 15 carbon atoms, and more preferably with from about 7 to about 12 carbon atoms, although the number of carbon atoms can be outside of these ranges, such as benzyl or the like, alkylaryl groups (including substituted alkylaryl groups), typically with from about 7 to about 30 carbon atoms, preferably with from about 7 to about 15 carbon atoms, and more preferably with from about 7 to about 12 carbon atoms, although the number of carbon atoms can be outside of these ranges, alkoxy groups (including substituted alkoxy groups, and wherein hetero atoms, such as oxygen, nitrogen, sulfur, silicon, phosphorus, and the like can be present in the alkoxy group), typically with from 1 to about 22 carbon atoms, preferably with from 1 to about 12 carbon atoms, and more preferably with from 1 to about 7 carbon atoms, although the number of carbon atoms can be outside of these ranges, polyalkyleneoxy groups (including substituted polyalkyleneoxy groups), such as polyethyleneoxy groups, polypropyleneoxy groups, polybutyleneoxy groups, and the like, typically with from about 3 to about 60 repeat alkyleneoxy units, preferably with from about 3 to about 30 repeat alkyleneoxy units, and more preferably with from about 3 to about 20 repeat alkyleneoxy units, although the number of repeat alkyleneoxy units can be outside of these ranges, wherein R' and R" can be joined together to form a ring, and wherein the substituents on the substituted alkyl, aryl, arylalkyl, alkylaryl, alkoxy, and polyalkyleneoxy groups can be (but are not limited to) hydroxy groups, amine groups, ammonium groups, pyridine groups, pyridinium groups, ether groups, ester groups, amide groups, carbonyl groups, mixtures thereof, and the like, wherein two or more substituents can be joined together to form a ring.

Borate esters prepared from beta-branched alcohols include those of the general formula:

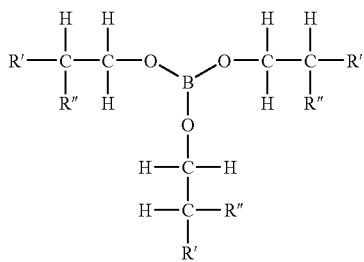

wherein R' and R" are as defined above for the beta-branched alcohols.

Some examples of borate esters prepared from beta-branched alcohols that are suitable for the present invention include, but are not limited to, borate esters of isobutyl alcohol, of the formula:

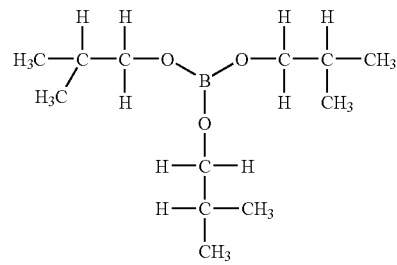

heteroborate esters of isobutyl alcohol and N,N-dibutylaminoethanol, of the formula:

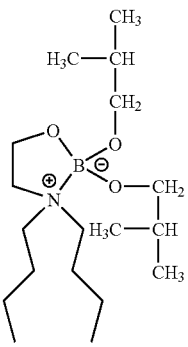

borate esters of polypropylene glycol, of the formula:

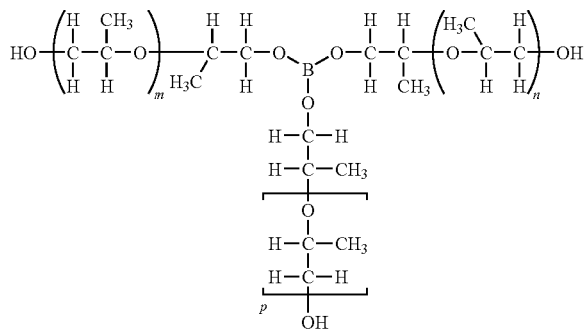

wherein m, n, and p are each, independently of the others, integers representing the number of repeat propylene oxide units, borate esters of propylene glycol/ethylene glycol copolymers, and the like.

During the reaction, the rotor 150 of FIG. 1 may be rotated between about 50 rpm and about 400 rpm, and temperature of the reactor body may be maintained between about 0° C. and about 25° C. Pressure within the reactor body may be maintained between about 266.6 Pa (about 2 Torr) and about 101.3 kPa (about 760 Torr).

In step 321, a stream of distillates from the reaction-distillation zone (such as acid products, such as HCl) may be removed from the vapor phase of the reaction-distillation zone, such as via distillation through an appropriate distillation apparatus, and may be recovered in a secondary step.

Step 320 comprises a residue neutralization stage wherein a base and solvent may be mixed with reaction products withdrawn from the reaction-distillation zone to neutralize residual acid product and to wash away any residual alcohol from the reaction. Suitable bases include OH-free bases such as, but are not limited to, alkali metal alkoxides, alkaline earth alkoxides, and amines, including, but not limited to, primary amines, secondary amines, tertiary amines, and heterocyclylalkylamines. Suitable amines may be selected from, but are not limited to, triethylamine, diisopropyl amine, trimethyl amine, tripropyl amine, tributylamine, and tert-butyl-methylamine.

In step 330 residual metal salts may be removed and useful metal salts from this step may be recirculated back to the reactive distillation process.

Step 340 comprises a precipitation and neutralization stage, wherein the metal alkoxide product may be precipitated, such as by the addition of anti-solvent. Following isolation of metal alkoxide product from step 340, recovered anti-solvent may be recirculated back into the process in step 323. Such anti-solvents may be any one of a number of non-polar solvents, or a mixture of any two or more thereof. For example, anti-solvents may include, but are not limited to acetone, alkanes such as pentane, hexane, or octane, benzene, toluene, tetrahydrofuran, diethyl ether, methyl-2-pentanone, methyl tert-butyl ether, methyl ethyl ketone, and/or mixtures of any two or more thereof.

Step 350 comprises a rinse stage, where metal alkoxide products may be rinsed with a solvent to remove remaining unreacted reactants, reaction solvents, and/or by-product residues. In step 323, solvent from step 350 may be recovered and recirculated back into the process.

Step 360 comprises a drying stage where the final product may be dried to remove residual solvent.

Figure 3:
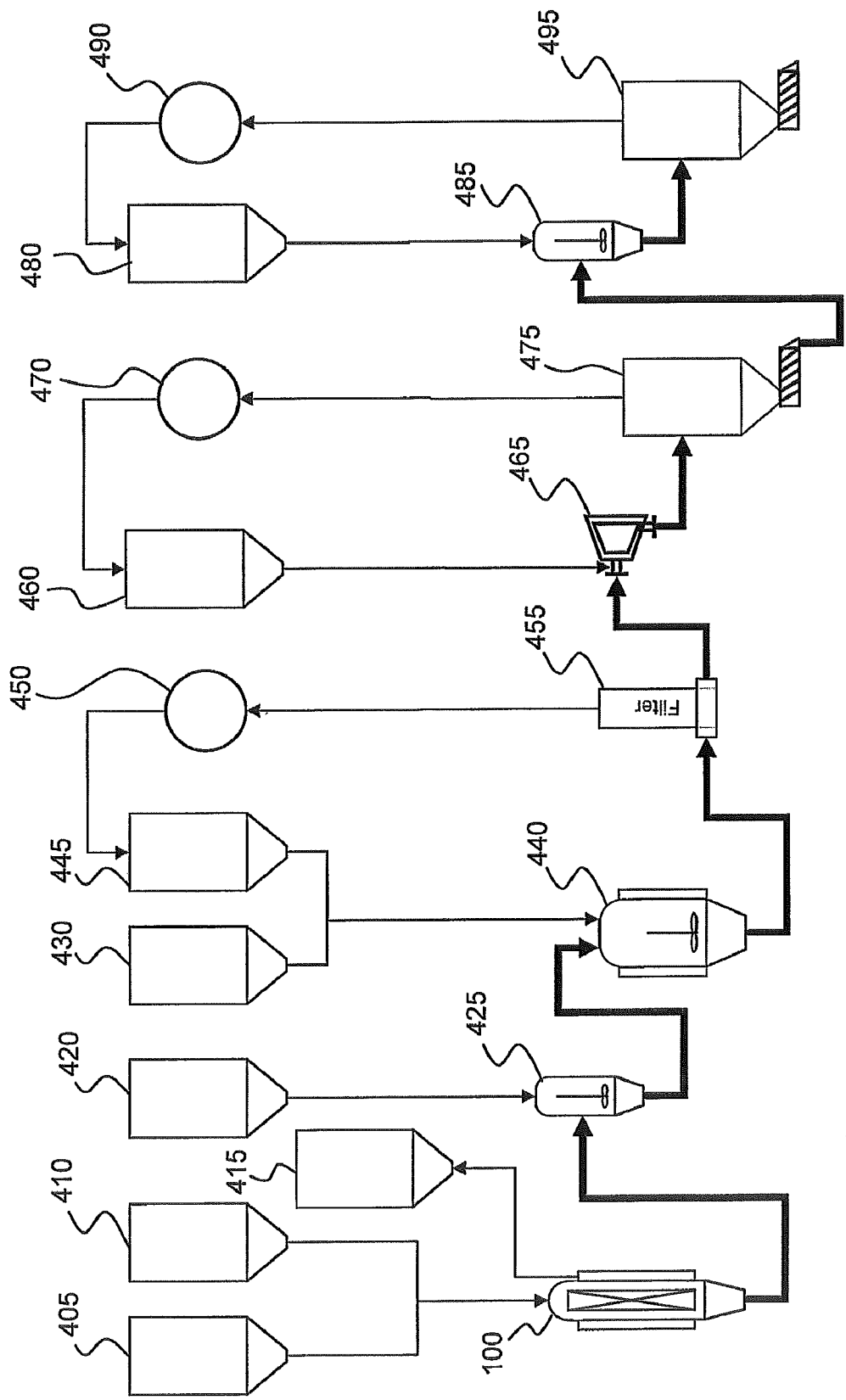
FIG. 3 is an illustration of a reaction system, in accordance with embodiments of the present invention.

FIG. 3 is an illustration of a reaction system 400. The reaction system 400 may be used to continuously reaction metal compounds to form metal alkoxides, such as those described above. The reaction system 400 may comprise an alcohol feed vessel 405 and a metal compound feed vessel 410, each operably connected to a reaction apparatus 100 such as the reaction apparatus described above and illustrated in FIG. 1. The alcohol feed vessel 405 may be configured to deliver an alcohol, such as alcohols described above, to the reaction apparatus 100. The metal compound feed vessel 410 may be configured to deliver a metal compound, such as those described above, to the reaction apparatus 100. The metal compound may be delivered in an alcohol solution, for example. The feed vessels described herein may each comprise appropriate metering devices and associated peripheral devices known in the art to accurately dispense materials in controlled and measured amounts and rates.

The reaction system 400 may comprise a vapor phase removal device 415 operably connected to the reaction apparatus 100 and configured to continuously remove reaction products from the vapor phase of the reaction-distillation zone of the reaction apparatus. For example, the vapor phase removal device 415 may comprise appropriate piping and at least one condenser configured to condense acid and water products being removed from the vapor phase. The vapor phase removal device 415 may comprise materials which are resistant to strong acids such as HCl, such as PTFE, stainless steel and other similar suitable materials described herein.

The reaction system 400 may comprise a mixing site 425 operably connected in line to the reaction apparatus 100. The mixing site may receive product withdrawn from the reaction apparatus 100 and mix the withdrawn product solution with a viscosity modifier. A viscosity modifier may be added to the product solution to improve flow of the product solution as it moves through the reaction system. The viscosity modifier may be added from a viscosity modifier feed vessel 420 connected to the mixing site 425. The mixing site may comprise a device configured such that the product and the viscosity modifier are sufficiently mixed. Such a device may comprise, for example, a vessel into which the two products enter, an inline injector introducing the viscosity modifier directly into a line carrying the withdrawn product, a static mixing device such as a series of baffles within a tube or channel through which the mixture of the withdrawn product and the viscosity modifier pass, a dynamic mixing device such as a powered blender, the like, or a combination thereof.

The reaction system 400 may comprise a precipitation/neutralization vessel 440 operatively connected in line to the reaction apparatus 100 and/or components there between, where the precipitation/neutralization vessel 440 may receive withdrawn reaction product there from. The precipitation/neutralization vessel 440 may be operatively connected to a solvent feed vessel 430 configured to deliver solvent to the precipitation/neutralization vessel 440 and/or a base feed vessel 445 configured to deliver base to the precipitation/neutralization vessel. The precipitation/neutralization vessel 440 may thus be used to wash residual alcohol from the withdrawn product solution and to neutralize residual acid product in the withdrawn product solution. The precipitation/neutralization vessel 440 may also be used to precipitate metal alkoxide product from solution using an appropriate solvent.

The reaction system 400 may comprise a decanter or filtration vessel 455 operably connected in line to the precipitation vessel 440 and/or components there between, where the filtration vessel 455 may receive withdrawn reaction product there from. The filtration vessel 455 may be configured to filter out base introduced in the precipitation vessel, where the filtered base may be delivered to a base recovery system 450 connected to the base feed vessel 445. The filtered base may then be returned to the base feed vessel 445 for reuse.

The reaction system 400 may comprise a high shear mixer 465 operably connected in line to the reaction apparatus 100 and/or components there between, where the high shear mixer 465 may receive withdrawn reaction product there from. An anti-solvent feed vessel 460 may be operably connect to the high shear mixer 465 and configured to deliver anti-solvent to the high shear mixer 465. The high shear mixer may comprise a device capable of high shear mixing such as a rotor/stationary stator mixer or a pressurized injection system. The high shear mixer may thus mix the withdrawn product with an anti-solvent and precipitate out metal alkoxide product as described above in step 340 of FIG. 2.

A powder isolation unit 475 may be operably connect inline to the high shear mixer 465, where the powder isolation unit 475 may receive a mixture comprising anti-solvent and precipitated metal alkoxides from the high shear mixer 465. The powder isolation unit may comprise a device configured to separate the solid precipitate from the anti-solvent, such as a spray dryer, a fluidized bed dryer, a thin film evaporator, a precipitation-filter unit, the like, or a combination thereof. The powder isolation unit 475 may separate the metal alkoxides product from the anti-solvent, where the anti-solvent may be recovered via an anti-solvent recovery system 470 operably connected to the powder isolation unit 475. The recovered anti-solvent may be returned to the anti-solvent feed system 460 for reuse.

The reaction system may comprise a solid wash vessel 485 operably connected in line to the reaction apparatus 100 and/or components there between, where the solids wash vessel 485 may receive withdrawn reaction product there from. The solids wash vessel 485 may comprise a device suitable for washing the solid product, such as to remove residual solvents or byproducts. The solid product may be washed with a solvent delivered from a solvent feed vessel 480 operably connected to the solids wash vessel and configured to deliver solvent to the solids feed vessel 480.

The reaction system 400 may comprise a product isolation unit 495 operably connected in line to the reaction apparatus 100 and/or components there between, where the product isolation unit 495 may receive reaction product there from and serves to collect and dry the solid powder product. The product isolation unit 495 may comprise a device configured to separate solvent from the solid precipitate, such as a spray dryer, a fluidized bed dryer, a thin film evaporator, a precipitation-filter unit, the like, or a combination thereof. Recovered solvent from the product isolation unit 495 may be recovered via a solvent recovery system 490 operably connected to the product isolation unit 495, where recovered solvent may be returned to the solvent feed vessel 480 connected to the solids wash vessel 485.

The following non-limiting examples illustrate certain aspects of the present invention.

Example 1

A solution of titanium oxychloride ($TiOCl_2$, 400 grams (g)), glycerol (400 g) and water (distilled, 400 g) was fed continuously by a metering pump into the reaction distillation zone at a rate of 1.75 liters/minute (L/min). Heating (at about 80° C.) under reduced pressure at about 98.2 kPa (about 29" Hg) gave rise to a vapor phase containing essentially water and about 20 to about 30% hydrochloric acid that was continually withdrawn and collected by vapor condensation. The viscous liquid phase product was continuously withdrawn from the reactor and treated to remove residual acid and excess glycerol. The resulting free flowing white powder product weighed about 340 g. Analysis of the product was consistent with titanyl glycerolates as confirmed by elemental analysis, $^1$H- and $^{13}$C-NMR.

Example 2

A solution of hydrated zinc acetate ($Zn(CH_3CO_2)_2*4H_2O$, 400 g), glycerol (400 g), and water (distilled, 400 g) is fed continuously by a metering pump into the reaction distillation zone at a rate of 1.75 L/min. Heating under reduced pressure evolves initially water then acetic acid vapors that are continually withdrawn and collected by vapor condensation. The viscous liquid phase product is continuously withdrawn from the reactor and treated to remove residual acid and excess glycerol. The resulting free flowing white powder product when analyzed will be consistent with zinc(II) glycerolate.

Example 3

A solution of hydrated manganese acetate ($Mn(CH_3CO_2)_2*2H_2O$, 400 g), glycerol (400 g), and water (distilled, 400 g) is fed continuously by a metering pump into the reaction distillation zone at a rate of 1.75 L/min. Heating under reduced pressure evolves initially water then acetic acid vapors that are continually withdrawn and collected by vapor condensation. The viscous liquid phase product is continuously withdrawn from the reactor and treated to remove residual acid and excess glycerol. The resulting pink powder product when analyzed will be consistent with manganese(II) glycerolate.

Example 4

A solution of hydrated cobalt acetate ($Co(CH_3CO_2)_2*4H_2O$, 400 g), glycerol (400 g), and water (distilled, 400 g) is fed continuously by a metering pump into the reaction distillation zone at a rate of 1.75 L/min. Heating under reduced pressure evolves initially water then acetic acid vapors that are continually withdrawn and collected by vapor condensation. The viscous liquid phase product is continuously withdrawn from the reactor and treated to remove residual acid and excess glycerol. The resulting mauve-colored powder product when analyzed will be consistent with cobalt(II) glycerolate.

Example 5

A solution of goethite ($\alpha$-FeO(OH), 400 g), glycerol (400 g), and water (distilled, 400 g) is fed continuously by a metering pump into the reaction distillation zone at a rate of 1.75 L/min. Heating under reduced pressure evolves water vapors that are continually withdrawn and collected by vapor condensation. The viscous liquid phase product is continuously withdrawn from the reactor and treated to remove excess glycerol. The resulting light-green product when analyzed will be consistent with iron glycerolates.

Example 6

A solution of boric acid ($B(OH)_3$, 400 g), glycerol (400 g), and water (distilled, 400 g) is fed continuously by a metering pump into the reaction distillation zone at a rate of 1.75 L/min. Heating under reduced pressure evolves water vapors that are continually withdrawn and collected by vapor condensation. The viscous liquid phase product is continuously withdrawn from the reactor and treated to remove excess glycerol. The resulting white product when analyzed will be consistent with diglyceryl borate.

Example 7

A solution of copper chloride ($CuCl_2$, 400 g), glycerol (400 g), and water (distilled, 400 g) is fed continuously by a metering pump into the reaction distillation zone at a rate of 1.75 L/min. Heating under reduced pressure evolves an acidic vapor stream that is continually withdrawn and collected by vapor condensation. The viscous liquid phase product is continuously withdrawn from the reactor and treated to remove residual acid and excess glycerol. The resulting light-green product when analyzed will be consistent with copper(II) glycerolate.

Example 8

A suspension of silver carbonate ($AgCO_3$, 400 g), glycerol (400 g), and water (distilled, 400 g) is fed continuously by a metering pump into the reaction distillation zone at a rate of 1.75 L/min. Heating under reduced pressure evolves a vapor stream that is continually withdrawn and collected by condensation. The viscous mixed-phase product is continuously withdrawn from the reactor and treated to remove excess glycerol. The resulting dark-brown product when analyzed will be consistent with silver glycerolates.

Example 9

A solution of zirconyl chloride ($ZrOCl_2$, 400 g), glycerol (400 g), and water (distilled, 400 g) is fed continuously by a metering pump into the reaction distillation zone at a rate of 1.75 L/min. Heating under reduced pressure evolves an acidic vapor stream that is continually withdrawn and collected by vapor condensation. The viscous liquid phase product is continuously withdrawn from the reactor and treated to remove residual acid and excess glycerol. The resulting white product when analyzed will be consistent with zirconyl glycerolates.

Example 10

A solution of nickel chloride (NiCl$_2$, 400 g), glycerol (400 g), and water (distilled, 400 g) is fed continuously by a metering pump into the reaction distillation zone at a rate of 1.75 L/min. Heating under reduced pressure evolves an acidic vapor stream that is continually withdrawn and collected by vapor condensation. The viscous liquid phase product is continuously withdrawn from the reactor and treated to remove residual acid and excess glycerol. The resulting light-green product when analyzed will be consistent with nickel(II) glycerolates.

Example 11

A solution of cobalt chloride (CoCl$_2$, 400 g), glycerol (400 g), and water (distilled, 400 g) is fed continuously by a metering pump into the reaction distillation zone at a rate of 1.75 L/min. Heating under reduced pressure evolves an acidic vapor stream that is continually withdrawn and collected by vapor condensation. The viscous liquid phase product is continuously withdrawn from the reactor and treated to remove residual acid and excess glycerol. The resulting magenta product when analyzed will be consistent with cobalt(II) glycerolates.

Example 12

A solution of titanium oxychloride (TiOCl$_2$, 400 g), glycerol (400 g) and water (distilled, 400 g) is fed continuously by a metering pump into the reaction distillation zone at a rate of 1.75 L/min. Heating (at about 80° C.) under reduced pressure of about 98.2 kPa (about 29" Hg) gives rise to a vapor phase containing water and hydrochloric acid that is continually withdrawn and collected by vapor condensation. The viscous liquid phase product is continuously withdrawn from the reactor and then heat at ambient pressure (at about 80° C.) with water (deionized, 400 g). After concentration under reduced pressure, the viscous liquid phase product is neutralized to remove residual acid and can then be washed to remove excess glycerol. The resulting white free-flowing powder, when analyzed by dynamic light scattering in ethanol solutions, will comprise particles of between 3 and 100 nm in size and is consistent with titanium glycerolate.

Example 13

A solution of chromium(III) chloride (CrCl$_3$, 400 g), glycerol (400 g), and water (distilled, 400 g) is fed continuously by a metering pump into the reaction distillation zone at a rate of 1.75 L/min. Heating under reduced pressure evolves an acidic vapor stream that is continually withdrawn and collected by vapor condensation. The green viscous liquid phase product is continuously withdrawn from the reactor and treated to remove residual acid and excess glycerol. The resulting green product when analyzed is consistent with chromium(III) glycerolates.

In Examples 14-19, the group 13 metal alkoxide flame retardants are synthesized in a continuous fashion by reactive distillation between a specific alcohol/polyol and group 13 (boron) trihydroxide. No catalyst is added, and heat and vacuum are used to remove water continuously from the reactor.

Example 14

N,N-dibutylethanolamine glycerol borate flame retardant is prepared as follows. Boric acid (10.3 grams), glycerol (15.3 grams), and N,N-dibutylethanolamine (28.9 grams) are fed into a wipe film reactor heated to 160° C. under a slight vacuum to remove the byproduct water (about 9 grams) continuously. The final product elutes from the reactor as a brownish viscous liquid product of N,N-dibutylethanolamine/glycerol borate.

Example 15

N,N-dibutylethanolamine sorbitol borate flame retardant is prepared as follows. Boric acid (10.3 grams), sorbitol (30.4 grams), and N,N-dibutylethanolamine (28.9 grams) are fed into a wipe film reactor heated to 160° C. under a slight vacuum to remove the byproduct water (about 9 grams) continuously. The final product elutes from the reactor as a yellowish resinous product of N,N-dibutylethanolamine/sorbitol borate.

Example 16

Salicylamide/glycerol borate flame retardant is prepared as follows. Boric acid (10.3 grams), glycerol (15.3 grams), and salicylamide (22.9 grams) are fed into a wipe film reactor heated to 160° C. under a slight vacuum and the byproduct water (about 9 grams) is continuously removed from the reaction zone. The final product elutes from the reactor as a yellowish resinous product of salicylamide/glycerol borate.

Example 17

Salicylamide/sorbitol borate flame retardant is prepared as follows. Boric acid (10.3 grams), sorbitol (30.4 grams), and salicylamide (22.9 grams) are fed into a wipe film reactor heated to 160° C. under a slight vacuum to remove byproduct water (about 9 grams) continuously. The final product elutes from the reactor as a yellowish resinous product of salicylamide/sorbitol borate.

Example 18

N,N-dibutylethanolamine/triethylene glycol monobutyl ether borate flame retardant is prepared as follows. Boric acid (10.3 grams), triethylene glycol monobutyl ether (Fluka, 64.1 grams), and N,N-dibutylethanolamine (28.9 grams) are fed into a wipe film reactor heated to 160° C. under a slight vacuum to remove the byproduct water (about 9 grams) continuously. The final product elutes from the reactor as a brownish liquid product of N,N-dibutylethanolamine/triethylene glycol monobutyl ether borate.

Example 19

N,N-dibutylethanolamine/poly(propylene glycol) monobutyl ether borate flame retardant is prepared as follows: Boric acid (10.3 grams), poly(propylene glycol) monobutyl ether (Aldrich, average $M_n$=340, 113.3 grams), and N,N-dibutylethanolamine (28.9 grams) are fed into a wipe film reactor heated to 160° C. under a slight vacuum to remove byproduct water (about 9 grams) continuously. The final product elutes from the reactor as a brownish liquid product of N,N-dibutylethanolamine/poly(propylene glycol) monobutyl ether borate.

In Examples 20-34, the group 13 metal alkoxide flame retardants were synthesized in a continuous fashion by reactive distillation between a specific alcohol/polyol and group 13 (boron or aluminum) trihydroxide. No catalyst was added, and heat and vacuum are used to remove water continuously from the reactor.

Example 20

Diglycerol borate flame retardant was prepared as follows: Boric acid (10.3 grams) and glycerol (30.6 grams) are fed into a wipe film reactor heated to 160° C. under a slight vacuum to remove byproduct water (about 9 grams) continuously. The final product eluted from the reactor as a clear viscous liquid product (about 30 grams) of diglycerol borate (Elemental Analysis Calculated, C, 37.54; H, 6.83; B, 5.63. Analyzed, C, 36.77; H, 6.68; B, 5.88).

Example 21

Dierythritol hydroxyborate flame retardant was prepared as follows: Boric acid (10.3 grams) and erythritol (15.3 grams) were added to a 250 milliliter round bottom flask. The reaction was heated to 160° C. under a slight vacuum to remove byproduct water (about 9 grams) continuously. The final product removed from the reactor was a clear viscous liquid product of dierythritol hydroxyborate (Elemental Analysis Calculated, C, 35.58; H, 7.09; B, 4.00. Analyzed, C, 35.43; H, 7.11; B, 3.98).

Example 22

Disorbitol hydroxyborate flame retardant was prepared as follows. Boric acid (10.3 grams) and sorbitol (15.3 grams) were added to a 250 milliliter round bottom flask. The reaction was heated to 160° C. under a slight vacuum to remove byproduct water (about 9 grams) continuously. The final product removed from the reactor was a clear viscous liquid product of disorbitol hydroxyborate (Elemental Analysis Calculated, C, 36.94; H, 6.98, B, 2.77. Analyzed, C, 38.58; H, 6.98, B, 2.78).

Example 23

Dixylitol hydroxyborate flame retardant was prepared as follows: Boric acid (25.6 grams) and xylitol (124.7 grams) were added to a 250 milliliter round bottom flask. The reaction was heated to 160° C. under a slight vacuum to remove byproduct water continuously. The final product removed from the reactor was a clear viscous liquid product of dixylitol hydroxyborate (Elemental Analysis Calculated, C, 36.39; H, 7.02; B, 3.28. Analyzed, C, 38.04; H, 6.72, B, 3.28).

Example 24

Dipentaerythritol hydroxyborate flame retardant was prepared as follows: Boric acid (10.3 grams) and xylitol (15.3 grams) were added to a 250 milliliter round bottom flask. The reaction was heated to 160° C. under a slight vacuum to remove byproduct water (about 9 grams) continuously. The final product removed from the reactor was a clear viscous liquid product of dixylitol hydroxyborate (Elemental Analysis Calculated, C, 40.29; H, 7.78, B, 3.63. Analyzed, C, 42.29; H, 7.64, B, 3.42).

Example 25

Hydroxyaluminum glycerolate flame retardant was prepared as follows: aluminum trihydroxide (51.08 grams) and glycerine (242.78 grams) were added to a 1 liter round bottom flask. The reaction was heated to 200° C. for one hour under a slight vacuum to remove byproduct water continuously. The final product removed from the reactor was a viscous white suspension of hydroxyaluminum glycerolate. Optionally, the solid can be collected by filtration. (Elemental Analysis Calculated, C, 26.88; H, 5.26, Al, 20.13. Analyzed, C, 22.58; H, 5.02, Al, 20.0), Infrared spectrum attached.

Example 26

Diglucosyl hydroxyborate flame retardant was prepared as follows: Boric acid (5.01 grams) and □-D-glucose (30.49 grams) were added to a 50 milliliter round bottom flask. The reaction was heated to 160° C. under a slight vacuum to remove byproduct water continuously. The final product removed from the reactor was a glassy solid product of diglucosyl hydroxyborate (Elemental Analysis Calculated, C, 37.33; H, 6.00, B: 2.80. Analyzed, C, 39.15; H, 5.71, B: 2.21), Infrared spectrum attached.

Example 27

((2R,3R,4S,5R)-3,4,5-trihydroxy-5-(hydroxymethyl)tetrahydrofuran-2-yl)methyl ((2S,3S,4R,5S)-3,4,5-trihydroxy-5-(hydroxymethyl)tetrahydrofuran-2-yl)methyl hydrogen borate flame retardant was prepared as follows: Boric acid (4.99 grams) and D-(−)-fructose (30.48 grams) were added to a 50 milliliter round bottom flask. The reaction was heated to 160° C. under a slight vacuum to remove byproduct water continuously. The final product removed from the reactor was a glassy solid product of ((2R,3R,4S,5R)-3,4,5-trihydroxy-5-(hydroxymethyl)tetrahydrofuran-2-yl)methyl ((2S,3S,4R,5S)-3,4,5-trihydroxy-5-(hydroxymethyl)tetrahydrofuran-2-yl)methyl hydrogen borate (Elemental Analysis Calculated, C, 37.33; H, 6.00, B, 2.80. Analyzed, C, 40.56; H, 5.48, B, 2.44), Infrared spectrum attached.

Example 28

A 3:2 Ribose:Borate flame retardant complex was prepared as follows: Boric acid (5.0 grams) and D-(−)-ribose (24.24 grams) were added to a 50 milliliter round bottom flask. The reaction was heated to 95° C. under a slight vacuum to remove byproduct water continuously. The final product removed from the reactor was a clear glassy solid product (Elemental Analysis Calculated, C, 35.89; H, 5.62, B, 4.31. Analyzed, C, 36.66; H, 5.14, B, 4.55).

Example 29

A cyclic triethanolamine borate flame retardant composition was prepared as follows: Boric acid (10.11 grams) and triethanolamine (25.03 grams) were added to a 50 milliliter round bottom flask. The reaction was heated to 80° C. under a slight vacuum to remove byproduct water continuously. The final product removed from the reactor was a fine white, hygroscopic solid product of 4,6,11-trioxa-1-aza-5-borabicyclo[3.3.3]undecane. (Elemental Analysis Calculated, C, 45.91; H, 7.71; N, 8.92; B, 6.89. Analyzed, C, 45.80; H, 7.70; N, 8.86; B, 5.36).

Example 30

Isooctyl alcohol/hexylene glycol aluminate ester flame retardant is prepared as follows. Aluminum trihydroxide (10.0 grams), isooctyl alcohol (5.84 grams), and hexylene glycol (20.1 grams) are fed into a wipe film reactor heated to 160° C. under a slight vacuum to remove the byproduct water continuously. The reactor residence time is adjusted so that the final aluminum product elutes from the reactor with a molar ratio comprising essentially 0.35 moles isooctyl alcohol per mole aluminum.

Example 31

Tridecyl alcohol/hexylene glycol aluminate ester flame retardant is prepared as follows. Aluminum trihydroxide (10.0 grams), tridecyl alcohol (6.42 grams), and hexylene glycol (20.9 grams) are fed into a wipe film reactor heated to 160° C. under a slight vacuum to remove the byproduct water continuously. The reactor residence time is adjusted so that the final aluminum product elutes from the reactor with a molar ratio comprising essentially 0.25 moles tridecyl alcohol per mole aluminum.

Example 32

Hexyl alcohol/hexylene glycol aluminate ester flame retardant is prepared as follows. Aluminum trihydroxide (10.0 grams), hexyl alcohol (1.64 grams), and hexylene glycol (21.8 grams) are fed into a wipe film reactor heated to 130° C. under a slight vacuum to remove the byproduct water continuously. The reactor residence time is adjusted so that the final aluminum product elutes from the reactor with a molar ratio comprising essentially 0.125 moles hexyl alcohol per mole aluminum.

Example 33

Compounding

A Theysohn TSK 21 mm Twin Screw Extruder was employed to formulate the Group 13 flame retardant compositions within the following matrices:

| Matrix | Flame Retardant | % Loading |
| --- | --- | --- |
| High impact polystyrene (HIPS) | Ex. 25 | 5.25 |
| High density polyethylene (HDPE) | Ex. 25 | 5.25 |
| Polybutyleneterephthalate (PBT) | Ex. 25 | 2.0 |
| Polyethyleneterephthalate (PET) | Ex. 25 | 2.0 |
| Acrylonitrile-butadiene-styrene (ABS) | Ex. 25 | 5.25 |
| Nylon 6 (N6) | Ex. 25 | 2.0 |
| Nylon 6 (N6) | Ex. 20 | 1.7 |

The extruder temperatures and feed rates were set according to the supplier's guidelines. Control pellets of Nylon 6 were collected without the flame retardant additive for comparative results. The pellets were then injection molded to prepare oxygen index level testing bars according to the type I dimensions of ASTM-D2863-08.

Example 34

Flame Retardant Performance

Oxygen index level testing was performed on the injection molded parts containing the flame retardant additives of Example 33. The oxygen index level for each polymer matrix was measurably higher than the control injection molded parts not containing the flame retardant additive. For example, the Nylon 6 containing the flame retardant additive prepared in accordance with Example 20 extruded part above loaded at 1.7% by weight giving a measured LOI (oxygen index level) of 25% $O_2$ concentration compared to the Nylon 6 control part processed without the flame retardant additive measuring 22% $O_2$ concentration.

The foregoing description of the embodiments of this invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the above described invention.

What is claimed is:

1. A method of preparing and purifying a product through a reaction distillation process comprising the steps of:
contacting a first amount of a metalloid or metal selected from a group consisting of Zinc and an element located in periodic table group 13-16 with a first amount of a polyol in a reaction-distillation zone in, a single, reaction apparatus and, resulting from said contacting, forming a metal alkoxide composition having the element located in periodic table group 13-16 contained therein, the metal alkoxide compound formed from a reaction of said element located in periodic table group 13-16 compound and said polyol;
simultaneously with said contacting, continuously removing reaction products from a vapor phase of said reaction-distillation zone; and
simultaneously with said contacting of said first amount of the metalloid or metal selected from a group consisting of Zinc and an element located in periodic table group 13-16 with first amount of the polyol in the reaction-distillation zone, continuously removing reaction products from a liquid phase of said reaction-distillation zone; and
modifying the metal alkoxide's flame retardant properties by adding a flame retardant additive to the metal alkoxide selected from a group consisting of a metal oxide ceramic, a thermoplastic, and a thermoset polymer.

2. The method of claim 1, wherein said contacting is continuous.

3. The method of claim 2, wherein said metalloid or metal selected from a group consisting of Zinc and an element located in periodic table group 13-16 is a periodic table group 13 metalloid or metal trihydroxide and said periodic table group 13 metalloid or metal is selected from the group consisting of boron, aluminum and combinations thereof.

4. The method of claim 1, wherein said polyol is selected from the group consisting of glycerol, sorbitol, xylitol, mannitol, glyceroloxyglycerol, 1,3-propanediol, triethylene glycol monomethyl ether, beta-branched alcohols, and combinations thereof.

5. A method of preparing and purifying a product through a reaction distillation process comprising the steps of:
contacting a first amount of a single transition metal compound and a first amount of an alcohol in a reaction-distillation zone of a single reaction apparatus and, resulting from said contacting, forming a transition metal alkoxide composition having only a single transition metal compound contained therein, the metal alkoxide compound formed from a reaction of said single transition metal compound and said alcohol within the single reaction apparatus;
simultaneously with said initial contacting, continuously removing reaction products from a vapor phase of said reaction-distillation;

simultaneously with said initial contacting, continuously removing reaction products from a liquid phase of said reaction-distillation zone; and modifying the metal alkoxide's flame retardant properties by adding a flame retardant additive to the metal alkoxide selected from a group consisting of a metal oxide ceramic, a thermoplastic, and a thermoset polymer.

6. The method of claim 5, wherein said transition metal is selected from the group consisting of titanium, zinc, manganese, cobalt, goethite, copper, silver, zirconium, nickel, chromium and combinations thereof.

7. The method of claim 1, having a periodic table group 13-16 metalloid or metal to alcohol ratio in the range of from 1 to 1 to about 1 to 6.

8. The method of claim 7, wherein the periodic table group 13-16 metalloid or metal to alcohol ratio is about 1 to 2.

9. The method of claim 5, having a transition metal to alcohol ratio in the range of from 1 to 1 to about 1 to 6.

10. The method of claim 5, wherein the transition metal to alcohol ratio is about 1 to 2.

11. The method of claim 5, wherein said alcohol is selected from the group consisting of: glycerol, sorbitol, xylitol, mannitol, glyceroloxyglycerol, 1,3-propanediol, triethylene glycol monomethyl ether, beta-branched alcohols, and combinations thereof.

12. A method of preparing and purifying a product through a reaction distillation process comprising:

forming, in a reaction-distillation zone of a single reaction apparatus, a metal alkoxide additive of the formula $[B(OH)_x(OR)_y]_n$, wherein $n>2$, $x+y=3$ and wherein $1 \geq x > 0$, and R independently comprises a substituted alkyl group, unsubstituted alkyl group, substituted aryl group, unsubstituted aryl group, and/or a combination thereof;

continuously removing reaction products from a vapor phase of the reaction-distillation zone;

continuously removing reaction products from a liquid phase of the reaction-distillation zone; and modifying the metal alkoxide's flame retardant properties by adding a flame retardant additive selected from a group consisting of a metal oxide ceramic, a thermoplastic, and a thermoset polymer.

* * * * *